United States Patent
Borrero et al.

(10) Patent No.: US 12,381,258 B2
(45) Date of Patent: Aug. 5, 2025

(54) FLUORINATED ELECTROLYTE ADDITIVES

(71) Applicant: E3TRIGEN, INC., Peachtree Corners, GA (US)

(72) Inventors: Nicholas Borrero, Augusta, GA (US); Neville Pavri, Evans, GA (US); Serguei Kovalenko, Martinez, GA (US)

(73) Assignee: E3TRIGEN, INC., Peachtree Corners, GA (US)

( * ) Notice: Subject to any disclaimer, the term of this patent is extended or adjusted under 35 U.S.C. 154(b) by 505 days.

(21) Appl. No.: 17/760,723

(22) PCT Filed: Sep. 17, 2020

(86) PCT No.: PCT/US2020/051207
§ 371 (c)(1),
(2) Date: Mar. 15, 2022

(87) PCT Pub. No.: WO2021/055560
PCT Pub. Date: Mar. 25, 2021

(65) Prior Publication Data
US 2022/0384848 A1 Dec. 1, 2022

Related U.S. Application Data

(60) Provisional application No. 62/901,553, filed on Sep. 17, 2019.

(51) Int. Cl.
*H01M 10/0567* (2010.01)
*C07C 68/065* (2020.01)
(Continued)

(52) U.S. Cl.
CPC ....... *H01M 10/0567* (2013.01); *C07C 68/065* (2013.01); *C07C 301/00* (2013.01);
(Continued)

(58) Field of Classification Search
CPC .. H01M 10/0567; H01M 4/364; H01M 4/386; H01M 4/505; H01M 4/525;
(Continued)

(56) References Cited

U.S. PATENT DOCUMENTS 2,968,667 A    1/1961   Lawlor
9,356,287 B2 * 5/2016   Kwon ................. H01M 10/052
(Continued)

FOREIGN PATENT DOCUMENTS

CN    102569890 A  *  7/2012
EP    2840642 A1       2/2015
(Continued)

OTHER PUBLICATIONS

Diethoxymethane. Database [online]. PubChem, [retrieved on Nov. 14, 2024]. Retrieved from the Internet: <URL: https://pubchem.ncbi.nlm.nih.gov/compound/Diethoxymethane>. (Year: 2024).*
(Continued)

*Primary Examiner* — Nicholas A Smith
*Assistant Examiner* — Kevin Nguyen
(74) *Attorney, Agent, or Firm* — Morgan, Lewis & Bockius LLP

(57) ABSTRACT

The disclosure relates to the use of fluorinated ethers such as 1,1,1,3,3,3-hexafluoro-2-methoxypropane (HFMOP) as a reaction solvent to prepare fluorinated dialkyl carbonate and sulfite compounds useful in batteries, and to electrolytes containing fluorinated compounds for use in batteries containing high Ni cathodes and silicon containing anodes.

20 Claims, 3 Drawing Sheets

(51) Int. Cl.
*C07C 301/00* (2006.01)
*H01M 4/36* (2006.01)
*H01M 4/38* (2006.01)
*H01M 4/505* (2010.01)
*H01M 4/525* (2010.01)
*H01M 4/587* (2010.01)
*H01M 10/0525* (2010.01)
*H01M 10/0568* (2010.01)
*H01M 10/0569* (2010.01)
*H01M 4/02* (2006.01)

(52) U.S. Cl.
CPC ........... *H01M 4/364* (2013.01); *H01M 4/386* (2013.01); *H01M 4/505* (2013.01); *H01M 4/525* (2013.01); *H01M 4/587* (2013.01); *H01M 10/0525* (2013.01); *H01M 10/0568* (2013.01); *H01M 10/0569* (2013.01); *H01M 2004/027* (2013.01); *H01M 2004/028* (2013.01); *H01M 2300/0034* (2013.01); *H01M 2300/0042* (2013.01)

(58) Field of Classification Search
CPC ............. H01M 4/587; H01M 10/0525; H01M 10/0568; H01M 10/0569; H01M 2004/027; H01M 2004/028; H01M 2300/0034; H01M 2300/0042; C07C 68/065; C07C 301/00
USPC ........................................................ 429/331
See application file for complete search history.

(56) References Cited

U.S. PATENT DOCUMENTS

| | | |
|---|---|---|
| 2008/0145763 A1 | 6/2008 | Koh et al. |
| 2013/0224605 A1 | 8/2013 | Lamanna et al. |
| 2015/0004501 A1* | 1/2015 | Koh ...................... H01M 4/505 429/200 |
| 2015/0191414 A1 | 7/2015 | Bomkamp et al. |
| 2015/0236380 A1 | 8/2015 | Garsuch et al. |
| 2018/0079708 A1 | 3/2018 | Dzwiniel et al. |
| 2018/0309169 A1 | 10/2018 | Yang et al. |
| 2019/0260079 A1 | 8/2019 | Zhu et al. |
| 2021/0135285 A1 | 5/2021 | Kim et al. |

FOREIGN PATENT DOCUMENTS

| | | | | |
|---|---|---|---|---|
| JP | 2002-343424 A | | 11/2002 | |
| JP | 2003-217656 A | | 7/2003 | |
| JP | 2004234949 A | * | 8/2004 | ............ B82Y 30/00 |
| JP | 2008-192504 A | | 8/2008 | |
| JP | 2008-277000 A | | 11/2008 | |
| JP | 2009-231283 A | | 10/2009 | |
| JP | 2014-078433 A | | 5/2014 | |
| JP | 2014-110235 A | | 6/2014 | |
| WO | 200138296 A1 | | 5/2001 | |
| WO | 2013/187180 A1 | | 12/2013 | |
| WO | 2019039763 A1 | | 2/2019 | |

OTHER PUBLICATIONS

NMC811. Datasheet [online]. Sigma Aldrich, [retrieved on May 1, 2025]. Retrieved from the Internet: <URL: https://www.sigmaaldrich.com/US/en/product/aldrich/934712?srsltid=AfmBOopKRUi7ladL8FV5bOSb-iaUjQfd6jBls36qI8EVMXH5f-LI2leK& icid=sharepdp-clipboard-copy-productdetailpagel>. (Year: 2025).*

International Search Report and Written Opinion dated Feb. 3, 2021 for International Patent Application No. PCT/US2020/051207, 11 pages.

Partial European Search Report for related European Patent Application No. EP 20864958.2, dated Dec. 20, 2024, 10 pages.

Japanese Office Action for related Japanese Patent Application No. 2022-542631, mailed Sep. 10, 2024, 9 pages.

* cited by examiner

FLUORINATED ELECTROLYTE ADDITIVES

CROSS-REFERENCE TO RELATED APPLICATIONS

This application is an International Patent Application which claims the benefit of U.S. Provisional Patent Application No. 62/901,553, filed Sep. 17, 2019, which is hereby incorporated by reference in its entirety.

FIELD

The disclosure relates to the use of fluorinated ethers such as 1,1,1,3,3,3-hexafluoro-2-methoxypropane (HFMOP) as a reaction solvent to prepare fluorinated dialkyl carbonate and sulfite compounds useful in batteries, and to batteries electrolytes including fluorinated dialkyl carbonate and sulfite compounds, and low levels of fluorinated ethers such as HFMOP. The use of fluorinated esters, carbonates and ethers as a component in the electrolyte to improve performance of electrochemical cells which incorporate high Ni cathodes, such as NMC 811 and anodes containing Si.

BACKGROUND

Lithium ion batteries are ubiquitous in our daily lives. There is a constant need to improve energy density for longer lasting and safer batteries.

Carbonate and sulfite compounds are used as electrolyte solvents and additives respectively for non-aqueous batteries with cathodes composed of alkali metals, alkaline earth metals, or materials composed thereof. For example, lithium ion batteries, which commonly use linear or cyclic carbonates such as dimethyl carbonate or ethylene carbonate. However, at battery voltages over 4.4 V, these compounds break down and battery performance suffers as a result.

SUMMARY

The disclosure provides methods for producing fluorinated compounds, including, without limitation, fluorinated organic carbonates and fluorinated organic sulfites. In some embodiments, the methods include reacting a first reactant including at least one fluorine atom with a second reactant of Formula 20A or Formula 20B, the reactant of Formula 20A or Formula 20B including a leaving group L:

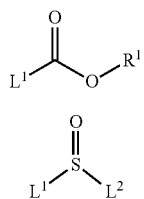

Formula 20A

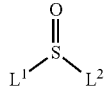

Formula 20B wherein: the reaction is performed in the presence of a fluorinated solvent; $R^1$ is selected from an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, and an optionally substituted haloheteroaryl; and $L^2$ is a leaving group. In some embodiments, the first reactant is a fluorinated alcohol. In some embodiments, the fluorinated organic carbonate is a fluorinated dialkyl carbonate. In some embodiments, the fluorinated organic sulfite is a fluorinated dialkyl sulfite. In some embodiments, the first reactant includes one or more groups selected from —$CF_3$, —$CHF_2$, —$CH_2F$, —CHF—, and —$CF_2$—. In some embodiments, the first reactant comprises one or more —$CF_3$ groups. In some embodiments, the first reactant is selected from 2-fluoroethanol, 2,2-difluoroethanol, 2,2,2-trifluoroethanol, 3-fluoro-1-propanol, 3,3-difluoro-1-propanol, 3,3,3-trifluoro-1-propanol, 2,2,3,3,3-pentafluoro-1-propanol, 1,1,1-trifluoro-2-propanol, 1,1,1,3,3-pentafluoro-2-propanol, 1,1,1,3,3,3-hexafluoro-2-propanol, 4,4,4-trifluoro-1-butanol, and 5,5,5-trifluoro-1-pentanol. In some embodiments, the first reactant is 1,1,1,3,3,3-hexafluoroisopropanol. In some embodiments, $L^1$ is selected from a perfluoroalkylsulfonate, a tosylate, a mesylate, a halogen, a nitrate, a phosphate, a thioether, an amine, a carboxylate, a phenoxide, an alkoxide, and an amide. In some embodiments, $L^1$ is selected from a halogen or an —$OR^2$ group. In some embodiments, $R^2$ is an alkyl sulfate or aryl sulfate. In some embodiments, $L^1$ is selected from chlorine, iodine, and bromine. In some embodiments, $L^2$ is selected from a perfluoroalkylsulfonate, a tosylate, a mesylate, a halogen, a nitrate, a phosphate, a thioether, an amine, a carboxylate, a phenoxide, an alkoxide, and an amide. In some embodiments, $L^2$ is selected from a halogen and an —$OR^3$ group. In some embodiments, $R^3$ is an alkyl sulfate or aryl sulfate. In some embodiments, $L^2$ is selected from chlorine, iodine, and bromine. In some embodiments, the compound of Formula 20A is a chloroformate. In some embodiments, the chloroformate is an alkyl chloroformate. In some embodiments, the chloroformate is methyl chloroformate or ethyl chloroformate. In some embodiments, the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate. In some embodiments, the compound of Formula 20B is thionyl chloride. In some embodiments, the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite. In some embodiments, the fluorinated solvent includes one or more groups selected from —$CF_3$, —$CHF_2$, —$CH_2F$, —CHF—, and —$CF_2$—. In some embodiments, the fluorinated solvent includes one or more —$CF_3$ groups. In some embodiments, the fluorinated solvent includes two or more —$CF_3$ groups.

In some embodiments, the fluorinated solvent is an ether or thioether having Formula 10:

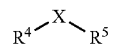

Formula 10 wherein X is O or S, $R^4$ is a partially fluorinated $C_1$-$C_8$ alkyl group; and $R^5$ is an optionally fluorinated $C_1$-$C_8$ alkyl group. In some embodiments, $R^4$ is a partially fluorinated $C_1$-$C_4$ alkyl group; and $R^5$ is an optionally fluorinated $C_1$-$C_4$ alkyl group. In some embodiments, the fluorinated solvent includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated solvent is hexafluoroisopropyl methyl ether. In some embodiments, the reaction is performed in the presence of an amine. In some embodiments, the amine is an alkylamine or a pyridine. In some embodiments, the alkyl amine is a trialkylamine. In some embodiments, the amine is selected from triethylamine, tripropylamine, tributylamine, diisopropylethylamine, pyridine, dimethylaminopyridine, 2,6-lutidine, and N,N-dimethylaniline. In some embodiments, the reaction is performed at a temperature between about −40° C. and about 80° C. In some embodiments, the reaction is performed at a temperature between about −40° C. and about 70° C. In some embodiments, the reaction is performed at a temperature between about 0° C. and about 35° C. In some embodiments, the reaction is performed at a temperature between about 10° C. and about 35° C.

The disclosure also provides a battery including an electrolyte including a fluorinated ether or thioether in an amount between about 1 ppm and about 5,000 ppm. In some embodiments, the battery is rechargeable, and wherein the battery has a cycle life of at least 250 cycles. In some embodiments, the fluorinated ether or thioether has Formula 10:

Formula 10 wherein X is O or S, $R^4$ is a partially fluorinated $C_1$-$C_8$ alkyl group; and $R^5$ is an optionally fluorinated $C_1$-$C_8$ alkyl group. In some embodiments, $R^4$ is a partially fluorinated $C_1$-$C_4$ alkyl group; and $R^5$ is an optionally fluorinated $C_1$-$C_4$ alkyl group. In some embodiments, the fluorinated ether or thioether includes one or more groups selected from —$CF_3$, —$CHF_2$, —$CH_2F$, —CHF—, and —$CF_2$—. In some embodiments, the fluorinated ether or thioether includes one or more —$CF_3$ groups. In some embodiments, the fluorinated ether includes two or more —$CF_3$ groups. In some embodiments, the fluorinated ether or thioether includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated ether or thioether is hexafluoroisopropyl methyl ether. In some embodiments, the battery is an alkali metal ion battery. In some embodiments, the battery is a lithium ion battery. In some embodiments, the electrolyte further includes a fluorinated organic carbonate or a fluorinated organic sulfite including one or more of an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, or an optionally substituted haloheteroaryl. In some embodiments, the fluorinated organic carbonate is a fluorinated dialkyl carbonate. In some embodiments, the fluorinated organic sulfite is a fluorinated dialkyl sulfite. In some embodiments, the fluorinated organic carbonate or the fluorinated organic sulfite includes one or more groups selected from —$CF_3$, —$CHF_2$, —$CH_2F$, —CHF—, and —$CF_2$—. In some embodiments, the fluorinated organic carbonate or the fluorinated organic sulfite includes one or more —$CF_3$ groups. In some embodiments, the fluorinated organic carbonate or the fluorinated organic sulfite includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated organic carbonate or the fluorinated organic sulfite includes one or two 1,1,1,3,3,3-hexafluoroisopropyl groups. In some embodiments, the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate. In some embodiments, the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

The disclosure also provides a battery comprising an electrolyte comprising a solvent component, wherein the solvent component comprises a fluorinated compound in an amount between about 1 ppm and about 60%, wherein the fluorinated compound has any one of Formula I, Formula II(a), Formula II(b), Formula III, or Formula IV:

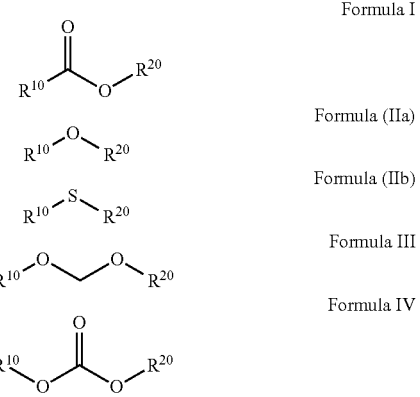

wherein $R^{10}$ and $R^{20}$ are independently selected from C1-C6 alkyl, C1-C8 alkyl, cycloalkyl, aryl, fully or partially fluorinated C1-C6 alkyl, fully or partially fluorinated C1-C8 alkyl, fully or partially fluorinated cycloalkyl, and fully or partially fluorinated aryl. In some embodiments, $R^{20}$ is a fully or partially fluorinated C1-C6 alkyl. In some embodiments, $R^{20}$ comprises one or more —$CF_3$ groups. In some embodiments, $R^{20}$ comprises one to three —$CF_3$ groups. In some embodiments, $R^{20}$ is selected from trifluoroethyl or hexafluoroisopropyl. In some embodiments, $R^{10}$ is selected from methyl, ethyl, n-propyl, and 2-propyl. In some embodiments, $R^{10}$ is selected from fully or partially fluorinated methyl, fully or partially fluorinated ethyl, fully or partially fluorinated n-propyl, and fully or partially fluorinated 2-propyl. In some embodiments, $R^{10}$ comprises one or more —$CF_3$ groups. In some embodiments, $R^{10}$ comprises one to three —$CF_3$ groups. In some embodiments, $R^{10}$ and $R^{20}$ are identical.

In some embodiments, the compound of Formula IV is a compound of any one of Formula 400, Formula 401, Formula 402, or Formula 403:

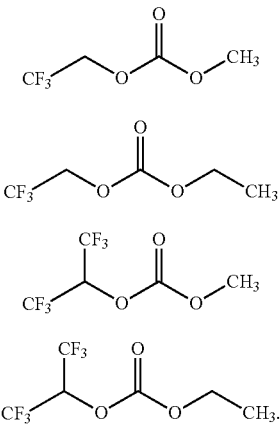

Formula 400

Formula 401

Formula 402

Formula 403

In some embodiments, the compound of Formula I is a compound of any one of Formula 100, Formula 101, Formula 102, or Formula 103:

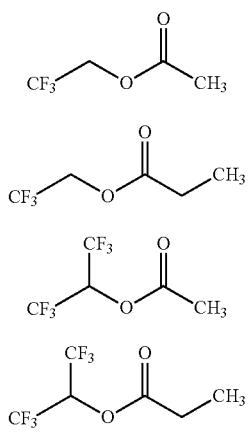

Formula 100

Formula 101

Formula 102

Formula 103

In some embodiments, the compound of Formula II(a) is a compound of any one of Formula 200, Formula 201, Formula 202, or Formula 203:

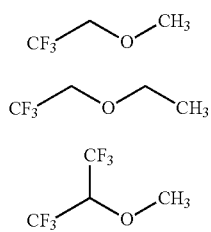

Formula 200

Formula 201

Formula 202

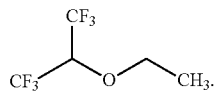

Formula 203

In some embodiments, the compound of Formula III is a compound of any one of Formula 300 or Formula 301:

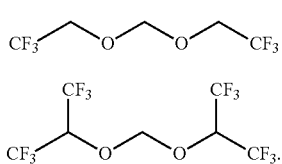

Formula 300

Formula 301

In some embodiments, the fluorinated compound is a an ether or thioether of Formula 10:

Formula 10 wherein in Formula 10 X is O or S, $R^4$ is a partially fluorinated $C_1$-$C_8$ alkyl group; and $R^5$ is an optionally fluorinated $C_1$-$C_8$ alkyl group.

In some embodiments, $R^4$ is a partially fluorinated $C_1$-$C_4$ alkyl group, and $R^5$ is an optionally fluorinated $C_1$-$C_4$ alkyl group. In some embodiments, the fluorinated ether or thioether comprises one or more groups selected from —$CF_3$, —$CHF_2$, —$CH_2F$, —CHF—, and —$CF_2$—. In some embodiments, the fluorinated ether or thioether comprises one or more —$CF_3$ groups. In some embodiments, the fluorinated ether or thioether comprises two or more —$CF_3$ groups. In some embodiments, the fluorinated ether or thioether comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated ether or thioether is hexafluoroisopropyl methyl ether.

In some embodiments, the solvent component comprises the fluorinated compound in an amount between about 1 ppm and about 5000 ppm. In some embodiments, the solvent component comprises the fluorinated compound in an amount between about 0.0001% and about 5%. In some embodiments, the solvent component comprises the fluorinated compound in an amount between about 0.1% and about 2%.

In some embodiments, wherein the electrolyte is a non-aqueous electrolyte, wherein the solvent component further comprises one or more of a partially fluorinated organic carbonate and non-fluorinated organic carbonate. In some embodiments, the non-fluorinated carbonate comprises one or more of EC (ethylene carbonate), EMC (ethyl methyl carbonate), DEC (diethyl carbonate), DMC (dimethyl carbonate), PC (propylene carbonate), and VC (vinylene carbonate or vinylidene carbonate). In some embodiments, the amount of VC in the solvent component is between about 0.001% and about 2%. In some embodiments, the partially fluorinated carbonate comprises FEC (fluoroethylene carbonate), wherein the amount of FEC in the solvent component is between about 0.001% and about 10%.

In some embodiments, the electrolyte further comprises a fluorinated organic carbonate or a fluorinated organic sulfite comprising one or more of an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, or an optionally substituted haloheteroaryl. In some embodiments, the fluorinated organic carbonate is a fluorinated dialkyl carbonate. In some embodiments, the fluorinated organic sulfite is a fluorinated dialkyl sulfite. In some embodiments, the fluorinated organic carbonate or the fluorinated organic sulfite comprises one or more groups selected from —$CF_3$, —$CHF_2$, —$CH_2F$, —CHF—, and —$CF_2$—. In some embodiments, the fluorinated organic carbonate or the fluorinated organic sulfite comprises one or more —$CF_3$ groups. In some embodiments, the fluorinated organic carbonate or the fluorinated organic sulfite comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated organic carbonate or the fluorinated organic sulfite comprises one or two 1,1,1,3,3,3-hexafluoroisopropyl groups.

In some embodiments, the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate. In some embodiments, the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

In some embodiments, the fluorinated organic carbonate is selected from ethyl (2,2,2-trifluoroethyl) carbonate, ethyl (1,1,1-trifluoroisopropyl) carbonate, ethyl (1,1,1,3,3,3-hexafluoroisopropyl) carbonate, ethyl (3,3,3-trifluoropropyl) carbonate, ethyl (2-fluoroethyl) carbonate, ethyl (2,2-difluoroethyl) carbonate, ethyl (3-fluoropropyl) carbonate, ethyl (3,3-difluoropropyl) carbonate, ethyl (2,2,3,3,3-pentafluoropropyl) carbonate, ethyl (4,4,4-trifluorobutyl) carbonate, ethyl (1,1,1,3,3-pentafluoroisopropyl) carbonate, and ethyl (5,5,5-trifluoropentyl) carbonate.

In some embodiments, the fluorinated organic carbonate is selected from n-propyl (2,2,2-trifluoroethyl) carbonate, n-propyl (1,1,1-trifluoroisopropyl) carbonate, n-propyl (1,1,1,3,3,3-hexafluoroisopropyl) carbonate, n-propyl (3,3,3-trifluoropropyl) carbonate, n-propyl (2-fluoroethyl) carbonate, n-propyl (2,2-difluoroethyl) carbonate, n-propyl (3-fluoropropyl) carbonate, n-propyl (3,3-difluoropropyl) carbonate, n-propyl (2,2,3,3,3-pentafluoropropyl) carbonate, n-propyl (4,4,4-trifluorobutyl) carbonate, n-propyl (1,1,1,3,3-pentafluoroisopropyl) carbonate, and n-propyl (5,5,5-trifluoropentyl) carbonate.

In some embodiments, the fluorinated organic carbonate is selected from isopropyl (2,2,2-trifluoroethyl) carbonate, isopropyl (1,1,1-trifluoroisopropyl) carbonate, isopropyl (1,1,1,3,3,3-hexafluoroisopropyl) carbonate, isopropyl (3,3,3-trifluoropropyl) carbonate, isopropyl (2-fluoroethyl) carbonate, isopropyl (2,2-difluoroethyl) carbonate, isopropyl (3-fluoropropyl) carbonate, isopropyl (3,3-difluoropropyl) carbonate, isopropyl (2,2,3,3,3-pentafluoropropyl) carbonate, isopropyl (4,4,4-trifluorobutyl) carbonate, isopropyl (1,1,1,3,3-pentafluoroisopropyl) carbonate, and isopropyl (5,5,5-trifluoropentyl) carbonate.

The disclosure also provides a battery including an electrolyte as described herein. In some embodiments, the electrolyte further comprises an alkaline salt. In some embodiments, the alkaline salt is dissolved in the solvent component, wherein the concentration of the alkaline salt is between about 1 M and about 1.5 M. In some embodiments, the alkaline salt is dissolved in the solvent component, wherein the concentration of the alkaline salt is about 1 M, about 1.1 M, about 1.2 M, about 1.3 M, about 1.4 M, or about 1.5 M. In some embodiments, the alkaline salt is a lithium salt. In some embodiments, the lithium salt is $LiPF_6$.

The disclosure also provides a battery including an anode and a cathode as described herein. In some embodiments, the cathode comprises a metal selected from nickel, manganese, and cobalt. In some embodiments, the cathode comprises between about 70% and about 90% nickel. In some embodiments, the cathode comprises between about 1% and about 15% manganese. In some embodiments, the cathode comprises between about 1% and about 15% cobalt. In some embodiments, the cathode comprises about 80% nickel, about 10% manganese, and about 10% cobalt. In some embodiments, the cathode comprises about 90% nickel, about 5% manganese, and about 5% cobalt. In some embodiments, the anode comprises between about 2% and about 75% silicon. In some embodiments, the anode comprises between about 2% and about 70% of a silicon oxide graphite composite. In some embodiments, the anode comprises between about 2% and about 70% of amorphous silicon graphite composite.

The disclosure also provides a battery as described herein, wherein the battery is rechargeable, and wherein the battery has a cycle life of between about 150 and about 500 cycles. In some embodiments, the battery has a cycle life of at least 200 cycles. In some embodiments, the battery has a cycle life of at least 250 cycles.

BRIEF DESCRIPTION OF THE DRAWINGS

The foregoing summary, as well as the following detailed description of the present disclosure, will be better understood when read in conjunction with the appended drawings.

DETAILED DESCRIPTION

Figure 1:
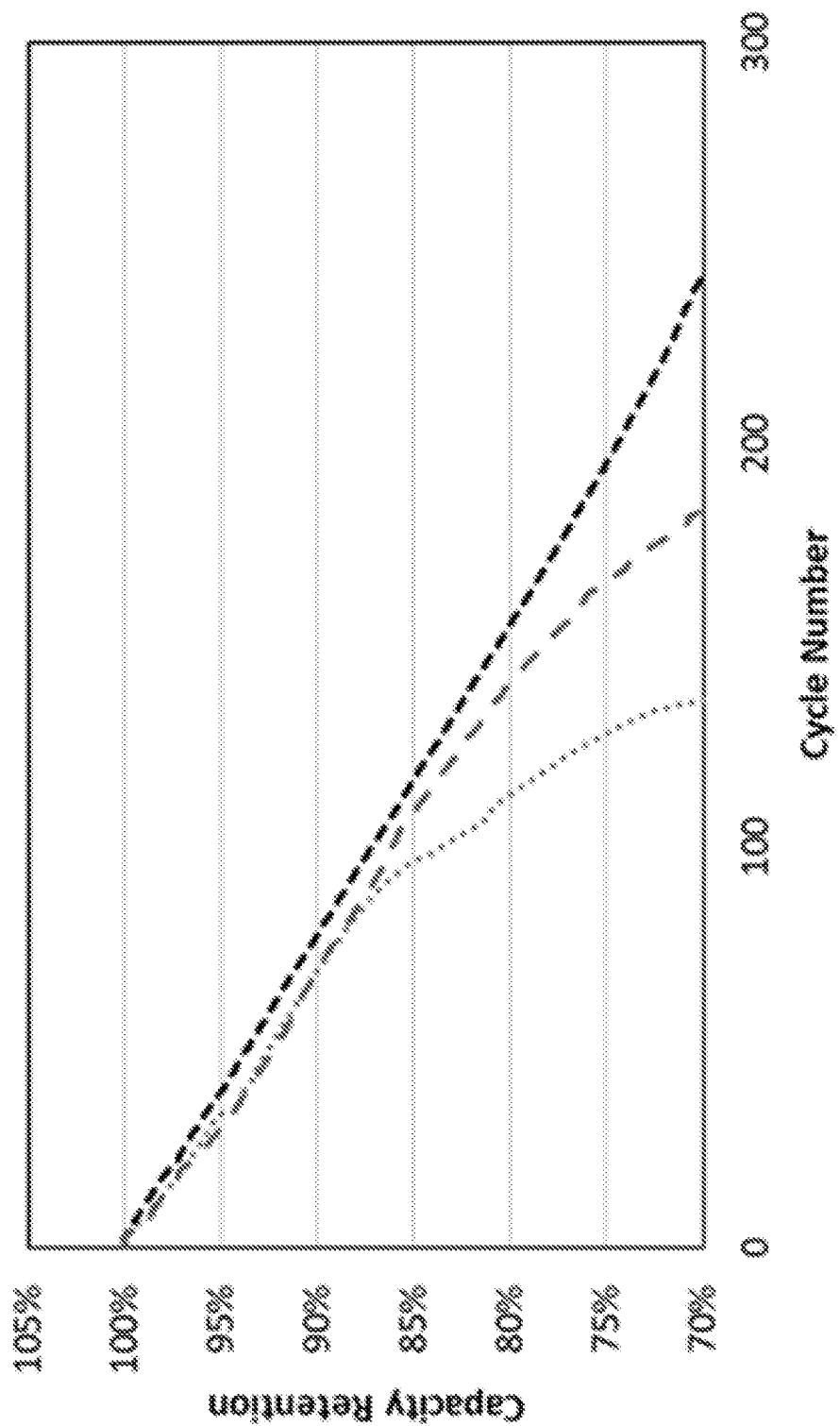
FIG. 1 illustrates the performance improvement at high temperature in a battery containing NMC 811 cathode and silicon composite anode by using trifluoroethyl methyl carbonate (F3EMC) as the fluorinated component of the electrolyte mixture, vs an electrolyte including fluoro ethylene carbonate (FEC).

There is great interest in using higher energy density electrodes such as silicon composite anodes and cathodes that are high nickel, for example NMC 811. Batteries made using high nickel NMC 811 and that incorporate silicon anodes are commercially relevant but still need improvements in performance. The main drawback is the breakdown of electrolyte in batteries of this type which result in poor cycling performance. Fluoroethylene carbonate (FEC) is widely used as an electrolyte additive or co-solvent in these systems to help generate SEI layer on Si composite anodes. The use of FEC has a serious drawback as it results in significant gassing in the cell which is a safety issue.

This disclosure provides for the use of other fluorinated carbonates, ethers and esters in combination with FEC in the electrolyte to further improve battery cycle life. The disclosure further provides for the use of trifluoromethylated carbonates in lieu of FEC, and/or in combination with FEC, resulting in significant improvements in cycle life.

In some embodiments, this disclosure provides an improved process to manufacture carbonates and sulfites with hexafluoroisopropyl methyl ether as solvent.

In some embodiments, this disclosure provides a battery comprising electrolyte containing fluorinated ether or thioether. In some embodiments, the amount of fluorinated ether or thioether in the electrolyte is between 1-5000 ppm. In some embodiments, the amount of fluorinated ether or thioether in the electrolyte is between 0.0001% and 2%. In some embodiments, these ethers include hexafluoroisopropyl methyl ether in an amount ranging between 1-5000 ppm. In some embodiments, these ethers include hexafluoroisopropyl methyl ether in amount ranging between 0.0001% and 2%. In some embodiments, the disclosure provides a battery comprising an electrolyte comprising bis(1,1,1,3,3,3-hexafluoroisopropyl) sulfite.

Methods for the manufacture of fluorinated carbonates are known in the art. U.S. Pat. App. No. 20120141870 discloses the preparation of methyl 2,2,2-trifluoroethyl carbonate in 46% yield whereby methyl chloroformate is added to a solution of 2,2,2-trifluoroethanol and pyridine in dichloromethane. U.S. Pat. App. No. 20180346404 discloses a similar process where dichloromethane is also used as solvent. Dichloromethane is disadvantageous for several reasons, including that traces of chlorine containing solvents will negatively impact battery performance should any be present in the final product, and dichloromethane is not recommendable for large scale processes due to toxicity. Furthermore, the yields obtained with dichloromethane are not ideal for large scale synthesis.

WO 2015083745 and WO 2015083747 describe the preparation of methyl 2,2,2-trifluoroethyl carbonate by adding methyl chloroformate to 2,2,2-trifluoroethanol and pyridine in triglyme, which may also carry over into the final product and be detrimental to the battery.

The preparation of fluorine-containing sulfites has also been reported (Journal of Fluorine Chemistry 6(1975) 93-104). In this process, the triethylamine adduct of a fluorinated alcohol is reacted with a fourfold excess of thionyl chloride at −78° C. The cryogenic temperatures and excess reactants required make the process unfavorable both practically and economically.

Unless defined otherwise, all technical and scientific terms used herein have the same meaning as is commonly understood by one of skill in the art to which this disclosure belongs. All patents and publications referred to herein are incorporated by reference in their entireties.

Definitions

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}C$ or $^{14}C$ enriched carbons, are within the scope of this disclosure.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, preferably from 0% to 10%, more preferably from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(N-R^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$ where each $R^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., ($C_{2-10}$)alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., ($C_{2-10}$)alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.
"Carboxyl" refers to a —(C=O)OH radical.
"Cyano" refers to a —CN radical.
"Cycloalkyl" refers to a monocyclic or polycyclic radical that contains only carbon and hydrogen, and may be saturated, or partially unsaturated. Cycloalkyl groups include groups having from 3 to 10 ring atoms (i.e. ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acylsulfonamide" refers a —S(O)$_2$—N(R$^a$)—C(=O)— radical, where R$^a$ is hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Unless stated otherwise specifically in the specification, an acylsulfonamide group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl "Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "aryloxy" refers to the group —O-aryl.

The term "substituted aryloxy" refers to aryloxy wherein the aryl substituent is substituted (i.e., —O-(substituted aryl)). Unless stated otherwise specifically in the specification, the aryl moiety of an aryloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" or "Het" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York (1981); E. L. Eliel, Stereochemistry of Carbon Compounds, McGraw-Hill, New York (1962); and E. L. Eliel and S. H. Wilen, Stereochemistry of Organic Compounds, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy, and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S— (optionally substituted alkyl), —S— (optionally substituted aryl), —S— (optionally substituted heteroaryl) and —S— (optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the disclosure also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

For the avoidance of doubt, it is intended herein that particular features (for example integers, characteristics, values, uses, diseases, formulae, compounds or groups) described in conjunction with a particular aspect, embodiment or example of the disclosure are to be understood as applicable to any other aspect, embodiment or example described herein unless incompatible therewith. Thus such features may be used where appropriate in conjunction with any of the definition, claims or embodiments defined herein. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any disclosed embodiments. The disclosure extends to any novel one, or novel combination, of the features disclosed in this specification (including any accompanying claims, abstract and drawings), or to any novel one, or any novel combination, of the steps of any method or process so disclosed.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed embodiments. All embodiments of the disclosure can, in the alternative, be more specifically defined by any of the transitional terms "comprising," "consisting essentially of," and "consisting of."

Fluorinated Solvent for Producing Fluorinated Compounds

The disclosure provides methods and processes for producing fluorinated dialkyl carbonates including but not limited to methyl 2,2,2-trifluoroethyl carbonate, methyl 1,1,1-trifluoroisopropyl carbonate, methyl 1,1,1,3,3,3-hexafluoroisopropyl carbonate, bis(2,2,2-trifluoroethyl) carbonate, bis(1,1,1-trifluoroisopropyl) carbonate, bis(1,1,1,3,3,3-hexafluoroisopropyl) carbonate, and fluorinated dialkyl sulfites including but not limited to bis(2,2,2-trifluoroethyl) sulfite, bis(1,1,1-trifluoroisopropyl) sulfite and bis(1,1,1,3,3,3-hexafluoroisopropyl) sulfite.

In the process of preparing fluorochemicals for application as solvents, co-solvents, and additives for high voltage lithium ion batteries, several issues were found during the synthesis, workup and purification of fluorinated carbonates on laboratory scale. Without wishing to be bound by any particular theory, it is believed that such issues can be addressed by judicious choice of solvent. In some embodiments, HFMOP was chosen, at least in part, due to its ability to control the exothermic effect for the particular chemical reactions involved, simplify workup, be removed easily, and be innocuous within the battery.

In some embodiments, the disclosure provides methods for producing fluorinated compounds, including, without limitation, fluorinated organic carbonates and fluorinated organic sulfites. In some embodiments, the methods include reacting a first reactant including at least one fluorine atom with a second reactant of Formula 20A or Formula 20B, the reactant of Formula 20A or Formula 20B including a leaving group $L^1$:

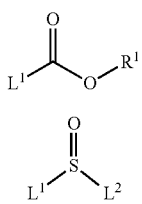

Formula 20A

Formula 20B wherein: the reaction is performed in the presence of a fluorinated solvent; $R^1$ is selected from an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, and an optionally substituted haloheteroaryl; and $L^2$ is a leaving group. In some embodiments, the first reactant is a fluorinated alcohol. In some embodiments, the fluorinated organic carbonate is a fluorinated dialkyl carbonate. In some embodiments, the fluorinated organic sulfite is a fluorinated dialkyl sulfite. In some embodiments, the first reactant includes one or more groups selected from —$CF_3$, —$CHF_2$, —$CH_2F$, —CHF—, and —$CF_2$—. In some embodiments, the first reactant comprises one or more —$CF_3$ groups. In some embodiments, the first reactant is selected from 2-fluoroethanol, 2,2-difluoroethanol, 2,2,2-trifluoroethanol, 3-fluoro-1-propanol, 3,3-difluoro-1-propanol, 3,3,3-trifluoro-1-propanol, 2,2,3,3,3-pentafluoro-1-propanol, 1,1,1-trifluoro-2-propanol, 1,1,1,3,3-pentafluoro-2-propanol, 1,1,1,3,3,3-hexafluoro-2-propanol, 4,4,4-trifluoro-1-butanol, and 5,5,5-trifluoro-1-pentanol. In some embodiments, the first reactant is 1,1,1,3,3,3-hexafluoroisopropanol. In some embodiments, $L^1$ is selected from a perfluoroalkylsulfonate, a tosylate, a mesylate, a halogen, a nitrate, a phosphate, a thioether, an amine, a carboxylate, a phenoxide, an alkoxide, and an amide. In some embodiments, $L^1$ is selected from a halogen or an —$OR^2$ group. In some embodiments, $R^2$ is an alkyl sulfate or aryl sulfate. In some embodiments, $L^1$ is selected from chlorine, iodine, and bromine. In some embodiments, $L^2$ is selected from a perfluoroalkylsulfonate, a tosylate, a mesylate, a halogen, a nitrate, a phosphate, a thioether, an amine, a carboxylate, a phenoxide, an alkoxide, and an amide. In some embodiments, $L^2$ is selected from a halogen and an —$OR^3$ group. In some embodiments, $R^3$ is an alkyl sulfate or aryl sulfate. In some embodiments, $L^2$ is selected from chlorine, iodine, and bromine. In some embodiments, the compound of Formula 20A is a chloroformate. In some embodiments, the chloroformate is an alkyl chloroformate. In some embodiments, the chloroformate is methyl chloroformate or ethyl chloroformate. In some embodiments, the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate. In some embodiments, the compound of Formula 20B is thionyl chloride. In some embodiments, the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite. In some embodiments, the fluorinated solvent includes one or more groups selected from —$CF_3$, —$CHF_2$, —$CH_2F$, —CHF—, and —$CF_2$—. In some embodiments, the fluorinated solvent includes one or more —$CF_3$ groups. In some embodiments, the fluorinated solvent includes two or more —$CF_3$ groups.

In some embodiments, the fluorinated solvent is an ether or thioether having Formula 10:

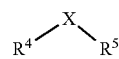

Formula 10 wherein X is O or S, $R^4$ is a partially fluorinated $C_1$-$C_8$ alkyl group; and $R^5$ is an optionally fluorinated $C_1$-$C_8$ alkyl group. In some embodiments, $R^4$ is a partially fluorinated $C_1$-$C_4$ alkyl group; and $R^5$ is an optionally fluorinated $C_1$-$C_4$ alkyl group. In some embodiments, the fluorinated solvent includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated solvent is hexafluoroisopropyl methyl ether (or 1,1,1,3,3,3-hexafluoro-2-methoxypropane):

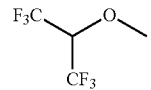

In some embodiments, the reaction is performed in the presence of an amine. In some embodiments, the amine is an alkylamine or a pyridine. In some embodiments, the alkyl amine is a trialkylamine. In some embodiments, the amine is selected from triethylamine, tripropylamine, tributylamine, diisopropylethylamine, pyridine, dimethylaminopyridine, 2,6-lutidine, and N,N-dimethylaniline. In some embodiments, the reaction is performed at a temperature between about −40° C. and about 80° C. In some embodiments, the reaction is performed at a temperature between about −40° C. and about 70° C. In some embodiments, the reaction is performed at a temperature between about 0° C. and about 35° C. In some embodiments, the reaction is performed at a temperature between about 10° C. and about 35° C.

As described herein, in some embodiments, synthesis involves addition of methyl chloroformate into fluorinated alcohol and triethylamine in a solvent, while controlling the exothermic effect with external cooling water to keep the internal temperature below 35° C. At the outset, tetraglyme (bp 275-276° C.) was employed to facilitate purification as the lower boiling point products should theoretically boil off first during distillation. However, and without wishing to be bound by any particular theory, it is believed that the relatively high heat capacity of tetraglyme makes controlling the exothermic effect difficult, resulting in a protracted addition time for methyl chloroformate (>3 hours). Using the methods and processes described herein, the cooling with water is more effective, and the addition time is reduced to approximately 1 h.

As described herein, in some embodiments, reaction workup entails neutralizing any remaining triethylamine and dissolving the triethylamine salt formed during the reaction with a dilute solution of hydrochloric acid. Without wishing to be bound by any particular theory, it is believed that tetraglyme is a solvent miscible with both the aqueous quench and the organic reaction components, making it difficult to remove water completely from the organic phase, and a water-free organic phase is important in order to avoid hydrolysis of the carbonate during subsequent distillation. Addition of a water immiscible co-solvents such as HFMOP, remedies this. In some embodiments, conducting the reaction itself in HFMOP obviates the need for a secondary solvent and allows for a simplified workup.

As described herein, in some embodiments, the purification step is accomplished by fractional distillation at atmospheric pressure. Without wishing to be bound by any particular theory, it is believed that low boiling HFMOP (bp 50° C.) is far more easily removed for recycling than high boiling solvents such as triglyme and tetraglyme. Moreover, fluorinated ethers such as HFMOP have been shown to provide benefits to cycle life in lithium ion batteries. Therefore, and without wishing to be bound by any particular theory, it is believed that any HFMOP carrying into the final product will not compromise battery performance unlike conventional solvents used to prepare these chemicals.

Similarly, HFMOP was employed in the synthesis of fluorinated alkyl sulfites. The reaction is previously reported as being conducted under solvent free conditions via the addition of thionyl chloride to a mixture of triethylamine and fluorinated alcohol at −78° C. The use of solvent is mitigated by the fact that the reaction can be conducted at ambient temperature with HFMOP, and the solvent is easily recovered for recycling. The reaction proceeds with the liberation of hydrogen chloride and is highly exothermic, however, the fluorinated ether is not acid labile in contrast to non-fluorinated ethers.

Battery Electrolytes Including Fluorinated Compounds

The rapid development of electronic devices has increased market demand for electrochemical devices such as fuel cells, capacitors, and battery systems. In response to the demand for battery systems in particular, practical rechargeable lithium batteries have been actively researched. These systems are typically based on the use of lithium metal, lithiated carbon, or a lithium alloy as the negative electrode (anode). Lithium batteries are prepared from one or more lithium electrochemical cells. Such cells include non-aqueous lithium ion-conducting electrolyte compositions interposed between electrically-separated, spaced-apart positive and negative electrodes.

An electrochemical cell comprises a housing, an anode and a cathode disposed in the housing and in ionically conductive contact with one another, an electrolyte composition, as described herein, providing an ionically conductive pathway between the anode and the cathode, and a porous or microporous separator between the anode and the cathode. The housing may be any suitable container to house the electrochemical cell components. The anode and the cathode may include any suitable conducting material depending on the type of electrochemical cell. Suitable examples of anode materials include without limitation lithium metal lithium metal alloys, lithium titanate, aluminum, platinum, palladium, graphite, transition metal oxides, and lithiated tin oxide. Suitable examples of cathode materials include without limitation graphite, aluminum, platinum, palladium, electroactive transition metal oxides comprising lithium or sodium, indium tin oxide, and conducting polymers such as polypyrrole and polyvinylferrocene.

The porous separator serves to prevent short circuiting between the anode and the cathode. The porous separator typically consists of a single-ply or multi-ply sheet of a microporous polymer such as polyethylene, polypropylene, or a combination thereof. The pore size of the porous separator is sufficiently large to permit transport of ions, but small enough to prevent contact of the anode and cathode either directly or from particle penetration or dendrites which can from on the anode and cathode.

In one embodiment, the electrochemical cell is a lithium ion battery, which is a type of rechargeable battery in which lithium ions move from the anode to the cathode during discharge, and from the cathode to the anode during charge. Suitable cathode materials for a lithium ion battery include without limitation electroactive transition metal oxides comprising lithium, such as $LiCoO_2$, $LiNiO_2$, $LiMn_2O_4$ or $LiV_3O_8$.

Various lithium composite oxides containing lithium and a transition metal may be utilized as the cathode material. Suitable examples include composite oxides with the general formula $LiMO_2$, where M can be any metallic elements or combination of metallic elements such as cobalt, aluminum, chromium, manganese, nickel, iron, vanadium, magnesium, titanium, zirconium, niobium, molybdenum, copper, zinc, indium, strontium, lanthanum, and cesium. Additionally, the active material can be made of a material with the chemical formula $LiMn_{2-x}M_xO_4$, where $0 \leq x \leq 1$, or a material with the general formula $LiMPO_4$ where M can be any metallic element or combination of elements such as cobalt, aluminum, chromium, manganese, nickel, iron, vanadium, magnesium, titanium, zirconium, niobium, molybdenum, copper, zinc, indium, strontium, lanthanum, and cesium. The cathode of the battery may include any of the active materials that may be held on an electrical conductive member that includes metal or another conductive element.

In one embodiment, the cathode in the lithium ion battery hereof comprises a cathode active material exhibiting greater than 30 mAh/g capacity in the potential range greater than 4.0 V, preferably (and in order of increasing preference) equal to or greater than 4.1 V, 4.2 V, 4.3 V, 4.4 V, 4.5 V, 4.25 V, 4.5 V, 4.6 V, or 4.75 V, versus a $Li/Li^+$ reference electrode. One example of such a cathode is a stabilized manganese cathode comprising a lithium-containing manganese composite oxide having a spinel structure as cathode active material. The lithium-containing manganese composite oxide in a cathode as used herein comprises oxides of the formula $Li_xNi_xM_zMn_{2-y-z}O_{4-d}$, wherein x is 0.03 to 1.0; x changes in accordance with release and uptake of lithium ions and electrons during charge and discharge; y is 0.3 to 0.6; M comprises one or more of Cr, Fe, Co, Al, Ga, Nb, Mo, Ti, Zr, Mg, Zn, V, and Cu; z is 0.01 to 0.18, and d is 0 to 0.3. In one embodiment, in the above formula, y is 0.38 to 0.48, z is 0.03 to 0.12, and d is 0 to 0.1. In one embodiment, in the above formula, M is one or more of Li, Cr, Fe, Co, and Ga. Stabilized manganese cathodes may also comprise spinel-layered composites which contain a manganese-containing spinel component and a lithium rich layered structure, as described in U.S. Pat. No. 7,303,840.

The cathode active material can be prepared using methods such as the hydroxide precursor method described by Liu et al (J. Phys. Chem., C 13:15073-15079, 2009). In that method, hydroxide precursors are precipitated from a solution containing the required amounts of manganese, nickel and other desired metal (s) acetates by the addition of KOH. The resulting precipitate is oven-dried and then fired with the required amount of $LiOH \cdot H_2O$ at about 800 to about 950° C. in oxygen for 3 to 24 hours. Alternatively, the cathode active material can be prepared using a solid phase reaction process or a sol-gel process as described in U.S. Pat. No. 5,738,957 (Amine).

The cathode, in which the cathode active material is contained, may be prepared by methods such as mixing an effective amount of the cathode active material (e.g. about 70 wt % to about 97 wt %), a polymer binder, such as polyvinylidene difluoride, and conductive carbon in a suitable solvent, such as N-methylpyrrolidone, to generate a paste, which is then coated onto a current collector such as aluminum foil, and dried to form the cathode.

The lithium ion battery further contains an anode, which comprises an anode active material that is capable of storing and releasing lithium ions. Examples of suitable anode active materials include without limitation lithium alloys such as lithium-aluminum alloy, lithium-lead alloy, lithium-silicon alloy, lithium-tin alloy and the like; carbon materials such as graphite and mesocarbon microbeads (MCMB); phosphorus-containing materials such as black phosphorus, $MnP_4$ and $CoP_3$; metal oxides such as $SnO_2$, $SnO$ and $TiO_2$; and lithium titanates such as $Li_4Ti_5O_{12}$ and $LiTi_2O_4$. In one embodiment, the anode active material is lithium titanate or graphite. An anode can be made by a method similar to that described above for a cathode wherein, for example, a binder such as a vinyl fluoride-based copolymer is dissolved or dispersed in an organic solvent or water, which is then mixed with the active, conductive material to obtain a paste. The paste is coated onto a metal foil, preferably aluminum or copper foil, to be used as the current collector. The paste is dried, preferably with heat, so that the active mass is bonded to the current collector. Suitable anode active materials and anodes are available commercially from companies such as Hitachi NEI Inc. (Somerset, N.J.), and Farasis Energy Inc. (Hayward, Calif.).

The lithium ion battery hereof also contains a porous separator between the anode and cathode. The porous separator serves to prevent short circuiting between the anode and the cathode. The porous separator typically consists of a single-ply or multi-ply sheet of a microporous polymer such as polyethylene, polypropylene, polyamide or polyimide, or a combination thereof. The separator can also be constructed using fluorinated polymers. The pore size of the porous separator is sufficiently large to permit transport of ions to provide ionically conductive contact between the anode and cathode, but small enough to prevent contact of the anode and cathode either directly or from particle penetration or dendrites which can from on the anode and cathode. Examples of porous separators suitable for use herein are disclosed in U.S. Patent Application Publication No. 2012/0149852.

The housing of the lithium ion battery hereof may be any suitable container to house the lithium ion battery components described above. Such a container may be fabricated in the shape of small or large cylinder, a prismatic case or a pouch.

The lithium ion battery hereof may be used in for any purpose and in any device which may be powered by lithium ion battery. Non-limiting examples of such purposes/devices include, i.e., grid storage or as a power source in various electronically powered or assisted devices such as a transportation device (including a motor vehicle, automobile, truck, bus or airplane), a computer, a telecommunications device, a camera, a radio, or a power tool.

In some embodiments, the electrolyte composition is typically a liquid solution of lithium electrolyte salt in a nonaqueous aprotic organic electrolyte solvent (often a solvent mixture). The selection of electrolyte solvents for rechargeable lithium batteries is crucial for optimal battery performance and involves a variety of different factors. However, long-term stability, ionic conductivity, safety, and wetting capability tend to be the most important selection factors in high volume commercial applications.

Fluorinated compounds, particularly esters, ethers, and carbonates have been utilized as constituents of electrolyte solutions used in electrochemical cells, and particularly in lithium batteries (both primary and secondary). Certain fluorinated compounds may offer several advantages over their non-fluorinated analogues, including reduced flammability, lower viscosity, improved wettability, greater oxidation/reduction resistance, and/or longer cycle times. These benefits are expected to be even more pronounced at voltages greater than about 4.0 V, and especially at higher voltages such as 4.3 V or higher, at which electrochemical potential such non-fluorinated analogues are particularly unstable.

In some embodiments, the disclosure provides a battery including an electrolyte including a fluorinated ether or thioether in an amount between about 1 ppm and about 5,000 ppm. Such amounts can typically be measured using a GC or GC/MS method. will In some embodiments, the amount of fluorinated ether or thioether in the electrolyte is between about 5 ppm and about 500 ppm, between about 25 ppm and about 750 ppm, between about 50 ppm and about 1,000 ppm, between about 100 ppm and about 1,500 ppm, between about 250 ppm and about 2,500 ppm, or between about 500 ppm and about 5,000 ppm.

In some embodiments, the battery is rechargeable, and wherein the battery has a cycle life of at least 250 cycles. As used herein, cycle life is the number of charge/discharge cycles it takes a battery to reach 80% of its original capacity. In some embodiments, the battery has a cycle life of at least 250 cycles, at least 500 cycles, at least 750 cycles, or at least 1,000 cycles. In some embodiments, the battery has a cycle life of at least 250 cycles, at least 300 cycles, at least 350 cycles, at least 400 cycles, at least 450 cycles, at least 500 cycles, at least 550 cycles, at least 600 cycles, at least 650 cycles, at least 700 cycles, at least 750 cycles, at least 800 cycles, at least 850 cycles, at least 900 cycles, at least 950 cycles, at least 1,000 cycles, at least 1,050 cycles, at least 1,100 cycles, at least 1,150 cycles, at least 1,200 cycles, at least 1,250 cycles, at least 1,300 cycles, at least 1,350 cycles, at least 1,400 cycles, at least 1,450 cycles, at least 1,500 cycles, at least 1,550 cycles, at least 1,600 cycles, at least 1,650 cycles, at least 1,700 cycles, at least 1,750 cycles, at least 1,800 cycles, at least 1,850 cycles, at least 1,900 cycles, at least 1,950 cycles, at least 2,000 cycles, at least 2,050 cycles, at least 2,100 cycles, at least 2,150 cycles, at least 2,200 cycles, at least 2,250 cycles, at least 2,300 cycles, at least 2,350 cycles, at least 2,400 cycles, at least 2,450 cycles, at least 2,500 cycles, at least 2,550 cycles, at least 2,600 cycles, at least 2,650 cycles, at least 2,700 cycles, at least 2,750 cycles, at least 2,800 cycles, at least 2,850 cycles, at least 2,900 cycles, at least 2,950 cycles, or at least 3,000 cycles.

In some embodiments, the fluorinated ether or thioether has Formula 10:

Formula 10 wherein X is O or S, $R^4$ is a partially fluorinated $C_1$-$C_8$ alkyl group; and $R^5$ is an optionally fluorinated $C_1$-$C_8$ alkyl group. In some embodiments, $R^4$ is a partially fluorinated $C_1$-$C_4$ alkyl group; and $R^5$ is an optionally fluorinated $C_1$-$C_4$ alkyl group. In some embodiments, the fluorinated ether or thioether includes one or more groups selected from —$CF_3$, —$CHF_2$, —$CH_2F$, —CHF—, and —$CF_2$—. In some embodiments, the fluorinated ether or thioether includes one or more —$CF_3$ groups. In some embodiments, the fluorinated ether or thioether includes two or more —$CF_3$ groups. In some embodiments, the fluorinated ether or thioether includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated ether or thioether is hexafluoroisopropyl methyl ether (or 1,1,1,3,3,3-hexafluoro-2-methoxypropane):

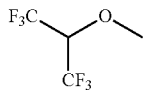

In some embodiments, the battery is an alkali metal ion battery. In some embodiments, the battery is a lithium ion battery. In some embodiments, the electrolyte further includes a fluorinated organic carbonate or a fluorinated organic sulfite including one or more of an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, or an optionally substituted haloheteroaryl. In some embodiments, the fluorinated organic carbonate is a fluorinated dialkyl carbonate. In some embodiments, the fluorinated organic sulfite is a fluorinated dialkyl sulfite. In some embodiments, the fluorinated organic carbonate or the fluorinated organic sulfite includes one or more groups selected from —$CF_3$, —$CHF_2$, —$CH_2F$, —CHF—, and —$CF_2$—. In some embodiments, the fluorinated organic carbonate or the fluorinated organic sulfite includes one or more —$CF_3$ groups. In some embodiments, the fluorinated organic carbonate or the fluorinated organic sulfite includes one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl. In some embodiments, the fluorinated organic carbonate or the fluorinated organic sulfite includes one or two 1,1,1,3,3,3-hexafluoroisopropyl groups. In some embodiments, the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate. In some embodiments, the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

The following clauses describe certain embodiments.

Clause 1. A method for producing a fluorinated organic carbonate or a fluorinated organic sulfite, the method comprising reacting a first reactant comprising at least one fluorine atom with a second reactant of Formula 20A or Formula 20B comprising a leaving group $L^1$.

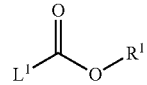

Formula 20A

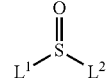

Formula 20B wherein: the reaction is performed in the presence of a fluorinated solvent; $R^1$ is selected from an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, and an optionally substituted haloheteroaryl; and $L^2$ is a leaving group.

Clause 2. The method of clause 1, wherein the first reactant is a fluorinated alcohol.

Clause 3. The method of clause 1, wherein the fluorinated organic carbonate is a fluorinated dialkyl carbonate.

Clause 4. The method of clause 1, wherein the fluorinated organic sulfite is a fluorinated dialkyl sulfite.

Clause 5. The method of any one of clauses 1 to 4, wherein the first reactant comprises one or more groups selected from —$CF_3$, —$CHF_2$, —$CH_2F$, —CHF—, and —$CF_2$—.

Clause 6. The method of any one of clauses 1 to 4, wherein the first reactant comprises one or more —$CF_3$ groups.

Clause 7. The method of any one of clauses 1 to 4, wherein the first reactant is selected from 2-fluoroethanol, 2,2-difluoroethanol, 2,2,2-trifluoroethanol, 3-fluoro-1-propanol, 3,3-difluoro-1-propanol, 3,3,3-trifluoro-1-propanol, 2,2,3,3,3-pentafluoro-1-propanol, 1,1,1-trifluoro-2-propanol, 1,1,1,3,3-pentafluoro-2-propanol, 1,1,1,3,3,3-hexafluoro-2-propanol, 4,4,4-trifluoro-1-butanol, and 5,5,5-trifluoro-1-pentanol.

Clause 8. The method of any one of clauses 1 to 4, wherein the first reactant is 1,1,1,3,3,3-hexafluoroisopropanol.

Clause 9. The method of any one of clauses 1 to 8, wherein $L^1$ is selected from a perfluoroalkylsulfonate, a tosylate, a mesylate, a halogen, a nitrate, a phosphate, a thioether, an amine, a carboxylate, a phenoxide, an alkoxide, and an amide.

Clause 10. The method of any one of clauses 1 to 8, wherein $L^1$ is selected from a halogen or an —$OR^2$ group.

Clause 11. The method of clause 10, wherein $R^2$ is an alkyl sulfate or aryl sulfate.

Clause 12. The method of any one of clauses 1 to 8, wherein $L^1$ is selected from chlorine, iodine, and bromine.

Clause 13. The method of any one of clauses 1 to 12, wherein $L^2$ is selected from a perfluoroalkylsulfonate, a tosylate, a mesylate, a halogen, a nitrate, a phosphate, a thioether, an amine, a carboxylate, a phenoxide, an alkoxide, and an amide.

Clause 14. The method of any one of clauses 1 to 12, wherein $L^2$ is selected from a halogen or an —$OR^3$ group.

Clause 15. The method of clause 14, wherein $R^3$ is an alkyl sulfate or aryl sulfate.

Clause 16. The method of any one of clauses 1 to 12, wherein $L^2$ is selected from chlorine, iodine, and bromine.

Clause 17. The method of any one of clauses 1 to 16, wherein the compound of Formula 20A is a chloroformate.

Clause 18. The method of clause 17, wherein the chloroformate is an alkyl chloroformate.

Clause 19. The method of clause 17, wherein the chloroformate is methyl chloroformate, ethyl chloroformate, n-propyl chloroformate, or 2-propyl chloroformate.

Clause 20. The method of any one of clauses 1 to 19, wherein the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate.

Clause 21. The method of any one of clauses 1 to 16, wherein the compound of Formula 20B is thionyl chloride.

Clause 22. The method of any one of clauses 1 to 19, or clause 21, wherein the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

Clause 23. The method of any one of clauses 1 to 22, wherein the fluorinated solvent comprises one or more groups selected from —$CF_3$, —$CHF_2$, —$CH_2F$, —CHF—, and —$CF_2$—.

Clause 24. The method of any one of clauses 1 to 22, wherein the fluorinated solvent comprises one or more —$CF_3$ groups.

Clause 25. The method of any one of clauses 1 to 22, wherein the fluorinated solvent comprises two or more —$CF_3$ groups.

Clause 26. The method of any one of clauses 1 to 25, wherein the fluorinated solvent is an ether or thioether having Formula 10:

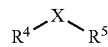

Formula 10 wherein X is O or S, $R^4$ is a fully or partially fluorinated $C_1$-$C_8$ alkyl group; and $R^5$ is an optionally fluorinated $C_1$-$C_8$ alkyl group.

Clause 27. The method of clause 26, wherein $R^4$ is a fully or partially fluorinated $C_1$-$C_4$ alkyl group; and $R^5$ is an optionally fluorinated $C_1$-$C_4$ alkyl group.

Clause 28. The method of any one of clauses 1 to 27, wherein the fluorinated solvent comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl.

Clause 28'. The method of any one of clauses 1 to 27, wherein the fluorinated solvent is hexafluoroisopropyl methyl ether.

Clause 29. The method of any one of clauses 1 to 28, wherein the reaction is performed in the presence of an amine.

Clause 30. The method of clause 29, wherein the amine is an alkylamine or a pyridine.

Clause 31. The method of clause 30, wherein the alkyl amine is a trialkylamine.

Clause 32. The method of clause 29, wherein the amine is selected from triethylamine, tripropylamine, tributylamine, diisopropylethylamine, pyridine, dimethylaminopyridine, 2,6-lutidine, and N,N-dimethylaniline.

Clause 33. The method of any one of clauses 1 to 32, wherein the reaction is performed at a temperature between about −40° C. and about 80° C.

Clause 34. The method of any one of clauses 1 to 32, wherein the reaction is performed at a temperature between about −40° C. and about 70° C.

Clause 35. The method of any one of clauses 1 to 32, wherein the reaction is performed at a temperature between about 0° C. and about 35° C.

Clause 36. The method of any one of clauses 1 to 32, wherein the reaction is performed at a temperature between about 10° C. and about 35° C.

Clause 37. A battery comprising an electrolyte comprising a solvent component, wherein the solvent component comprises a fluorinated compound in an amount between about 1 ppm and about 60%, wherein the fluorinated compound has any one of Formula I, Formula II(a), Formula II(b), Formula III, or Formula IV:

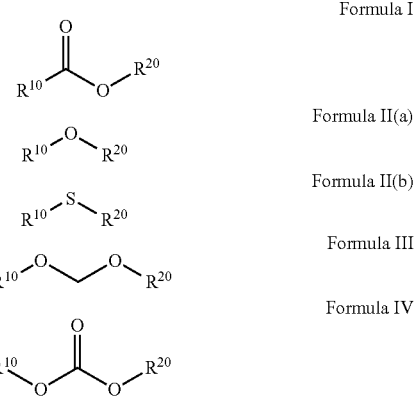

wherein $R^{10}$ and $R^{20}$ are independently selected from C1-C6 alkyl, cycloalkyl, aryl, fully or partially fluorinated C1-C6 alkyl, fully or partially fluorinated cycloalkyl, and fully or partially fluorinated aryl.

Clause 38. The battery of clause 37, wherein $R^{20}$ is a fully or partially fluorinated C1-C6 alkyl.

Clause 39. The battery of clause 37, wherein $R^{20}$ comprises one or more —$CF_3$ groups.

Clause 40. The battery of clause 37, wherein $R^{20}$ comprises one to three —$CF_3$ groups.

Clause 41. The battery of clause 37, wherein $R^{20}$ is selected from trifluoroethyl or hexafluoroisopropyl.

Clause 42. The battery of any one of clauses 37 to 41, wherein $R^{10}$ is selected from methyl, ethyl, n-propyl, and 2-propyl.

Clause 43. The battery of any one of clauses 37 to 41, wherein $R^{10}$ is selected from fully or partially fluorinated methyl, fully or partially fluorinated ethyl, fully or partially fluorinated n-propyl, and fully or partially fluorinated 2-propyl.

Clause 44. The battery of any one of clauses 37 to 41, wherein $R^{10}$ comprises one or more —$CF_3$ groups.

Clause 45. The battery of any one of clauses 37 to 41, wherein $R^{10}$ comprises one to three —$CF_3$ groups.

Clause 46. The battery of clause 37, wherein $R^{10}$ and $R^{20}$ are identical.

Clause 47. The battery of clause 37, wherein the compound of Formula IV is a compound of any one of Formula 400, Formula 401, Formula 402, or Formula 403:

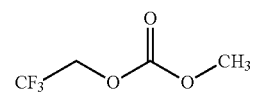

Formula 400

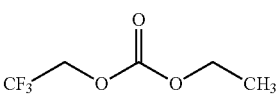

Formula 401

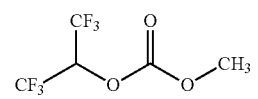

Formula 402

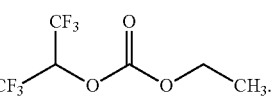

Formula 403

Clause 48. The battery of clause 37, wherein the compound of Formula I is a compound of any one of Formula 100, Formula 101, Formula 102, or Formula 103:

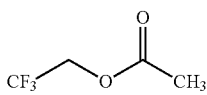

Formula 100

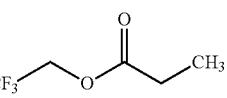

Formula 101

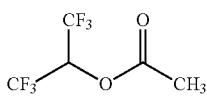

Formula 102

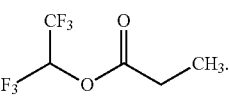

Formula 103

Clause 49. The battery of clause 37, wherein the compound of Formula II(a) is a compound of any one of Formula 200, Formula 201, Formula 202, or Formula 203:

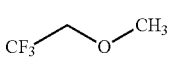

Formula 200

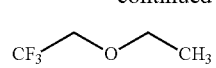

Formula 201

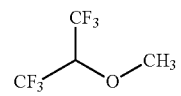

Formula 202

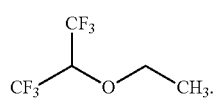

Formula 203

Clause 50. The battery of clause 37, wherein the compound of Formula III is a compound of any one of Formula 300 or Formula 301:

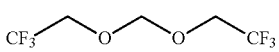

Formula 300

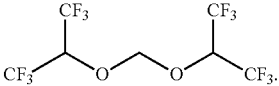

Formula 301

Clause 51. The battery of clause 37, wherein the fluorinated compound is a an ether or thioether of Formula 10:

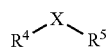

Formula 10 wherein in Formula 10 X is O or S, $R^4$ is a partially fluorinated $C_1$-$C_8$ alkyl group; and $R^5$ is an optionally fluorinated $C_1$-$C_8$ alkyl group.

Clause 52. The battery of clause 51, wherein $R^4$ is a partially fluorinated $C_1$-$C_4$ alkyl group, and $R^5$ is an optionally fluorinated $C_1$-$C_4$ alkyl group.

Clause 53. The battery of any one of clauses 51 or 52, wherein the fluorinated ether or thioether comprises one or more groups selected from —$CF_3$, —$CHF_2$, —$CH_2F$, —CHF—, and —$CF_2$—.

Clause 54. The battery of any one of clauses 51 to 53, wherein the fluorinated ether or thioether comprises one or more —$CF_3$ groups.

Clause 55. The battery of any one of clauses 51 to 53, wherein the fluorinated ether or thioether comprises two or more —$CF_3$ groups.

Clause 56. The battery of any one of clauses 51 to 55, wherein the fluorinated ether or thioether comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl.

Clause 57. The battery of any one of clauses 51 to 55, wherein the fluorinated ether or thioether is hexafluoroisopropyl methyl ether.

Clause 58. The battery of any one of clauses 37 to 57, wherein the solvent component comprises the fluorinated compound in an amount between about 1 ppm and about 5000 ppm. In some embodiments, the solvent component comprises the fluorinated compound in an amount between about 1 ppm and about 100 ppm. In some embodiments, the solvent component comprises the fluorinated compound in an amount between about 100 ppm and about 500 ppm. In some embodiments, the solvent component comprises the fluorinated compound in an amount between about 500 ppm and about 1000 ppm. In some embodiments, the solvent component comprises the fluorinated compound in an amount between about 1000 ppm and about 2000 ppm. In some embodiments, the solvent component comprises the fluorinated compound in an amount between about 2000 ppm and about 3000 ppm. In some embodiments, the solvent component comprises the fluorinated compound in an amount between about 3000 ppm and about 4000 ppm. In some embodiments, the solvent component comprises the fluorinated compound in an amount between about 4000 ppm and about 5000 ppm. In some embodiments, the solvent component comprises the fluorinated compound in an amount between about 5000 ppm and about 7500 ppm. In some embodiments, the solvent component comprises the fluorinated compound in an amount between about 7500 ppm and about 10000 ppm.

Clause 59. The battery of any one of clauses 37 to 57, wherein the solvent component comprises the fluorinated compound in an amount between about 0.0001% and about 5%. In some embodiments, the solvent component comprises the fluorinated compound in an amount between about 0.0001% and about 10%. In some embodiments, the solvent component comprises the fluorinated compound in an amount between about 0.0001% and about 15%. In some embodiments, the solvent component comprises the fluorinated compound in an amount between about 0.001% and about 0.01%. In some embodiments, the solvent component comprises the fluorinated compound in an amount between about 0.01% and about 0.1%. In some embodiments, the solvent component comprises the fluorinated compound in an amount between about 0.1% and about 1%. In some embodiments, the solvent component comprises the fluorinated compound in an amount between about 1% and about 2%. In some embodiments, the solvent component comprises the fluorinated compound in an amount between about 2% and about 3%. In some embodiments, the solvent component comprises the fluorinated compound in an amount between about 3% and about 4%. In some embodiments, the solvent component comprises the fluorinated compound in an amount between about 4% and about 5%. In some embodiments, the solvent component comprises the fluorinated compound in an amount between about 5% and about 6%. In some embodiments, the solvent component comprises the fluorinated compound in an amount between about 6% and about 7%. In some embodiments, the solvent component comprises the fluorinated compound in an amount between about 7% and about 8%. In some embodiments, the solvent component comprises the fluorinated compound in an amount between about 8% and about 9%. In some embodiments, the solvent component comprises the fluorinated compound in an amount between about 9% and about 10%. In some embodiments, the solvent component comprises the fluorinated compound in an amount between about 10% and about 20%. In some embodiments, the solvent component comprises the fluorinated compound in an amount between about 10% and about 30%. In some embodiments, the solvent component comprises the fluorinated compound in an amount between about 30% and about 40%. In some embodiments, the solvent component comprises the fluorinated compound in an amount between about 40% and about 50%. In some embodiments, the solvent component comprises the fluorinated compound in an amount between about 50% and about 60%.

Clause 60. The battery of any one of clauses 37 to 57, wherein the solvent component comprises the fluorinated compound in an amount between about 0.1% and about 2%. In some embodiments, the solvent component comprises the fluorinated compound in an amount between about 0.1% and about 0.5%. In some embodiments, the solvent component comprises the fluorinated compound in an amount between about 0.5% and about 1%. In some embodiments, the solvent component comprises the fluorinated compound in an amount between about 1% and about 1.5%. In some embodiments, the solvent component comprises the fluorinated compound in an amount between about 1.5% and about 2%. In some embodiments, the solvent component comprises the fluorinated compound in an amount between about 2% and about 2.5%. In some embodiments, the solvent component comprises the fluorinated compound in an amount between about 2.5% and about 3%. In some embodiments, the solvent component comprises the fluorinated compound in an amount between about 3% and about 3.5%. In some embodiments, the solvent component comprises the fluorinated compound in an amount between about 3.5% and about 4%. In some embodiments, the solvent component comprises the fluorinated compound in an amount between about 4% and about 4.5%. In some embodiments, the solvent component comprises the fluorinated compound in an amount between about 4.5% and about 5%.

Clause 61. The battery of any one of clauses 37 to 60, wherein the electrolyte is a non-aqueous electrolyte, wherein the solvent component further comprises one or more of a partially fluorinated organic carbonate and non-fluorinated organic carbonate.

Clause 62. The battery of clause 58, wherein the non-fluorinated carbonate comprises one or more of EC (ethylene carbonate), EMC (ethyl methyl carbonate), DEC (diethyl carbonate), DMC (dimethyl carbonate), PC (propylene carbonate), and VC (vinylene carbonate and/or vinylidene carbonate).

Clause 63. The battery of clause 62, wherein the amount of VC in the solvent component is between about 0.001% and about 2%. In some embodiments, the amount of VC in the solvent component is between about 0.001% and about 0.01%. In some embodiments, the amount of VC in the solvent component is between about 0.01% and about 0.1%. In some embodiments, the amount of VC in the solvent component is between about 0.1% and about 0.5%. In some embodiments, the amount of VC in the solvent component is between about 0.5% and about 1%. In some embodiments, the amount of VC in the solvent component is between about 1% and about 2%. In some embodiments, the amount of VC in the solvent component is between about 2% and about 3%. In some embodiments, the amount of VC in the solvent component is between about 3% and about 4%. In some embodiments, the amount of VC in the solvent component is between about 4% and about 5%.

Clause 64. The battery of clause 61, wherein the partially fluorinated carbonate comprises FEC (fluoroethylene carbonate), wherein the amount of FEC in the solvent component is between about 0.001% and about 10%. In some embodiments, the amount of FEC in the solvent component is between about 0.001% and about 15%. In some embodiments, the amount of FEC in the solvent component is between about 1% and about 25%. In some embodiments, the amount of FEC in the solvent component is between about 0.01%% and about 10%. In some embodiments, the amount of FEC in the solvent component is between about 1% and about 10%. In some embodiments, the amount of FEC in the solvent component is between about 0.01% and about 9%. In some embodiments, the amount of FEC in the solvent component is between about 0.01% and about 8%. In some embodiments, the amount of FEC in the solvent component is between about 0.01% and about 7%. In some embodiments, the amount of FEC in the solvent component is between about 0.01% and about 6%. In some embodiments, the amount of FEC in the solvent component is between about 0.01% and about 5%. In some embodiments, the amount of FEC in the solvent component is between about 5% and about 10%. In some embodiments, the amount of FEC in the solvent component is between about 10% and about 15%. In some embodiments, the amount of FEC in the solvent component is between about 15% and about 20%. In some embodiments, the amount of FEC in the solvent component is between about 20% and about 25%. In some embodiments, the solvent component does not include FEC.

Clause 65. The battery of any one of clauses 37 to 60, wherein the electrolyte further comprises a fluorinated organic carbonate or a fluorinated organic sulfite comprising one or more of an optionally substituted alkyl, an optionally substituted haloalkyl, an optionally substituted alkenyl, an optionally substituted haloalkenyl, an optionally substituted alkynyl, an optionally substituted haloalkynyl, an optionally substituted aryl, an optionally substituted haloaryl, an optionally substituted heteroaryl, or an optionally substituted haloheteroaryl.

Clause 66. The battery of clause 65, wherein the fluorinated organic carbonate is a fluorinated dialkyl carbonate.

Clause 67. The battery of clause 65, wherein the fluorinated organic sulfite is a fluorinated dialkyl sulfite.

Clause 68. The battery of any one of clauses 65 to 67, wherein the fluorinated organic carbonate or the fluorinated organic sulfite comprises one or more groups selected from —$CF_3$, —$CHF_2$, —$CH_2F$, —CHF—, and —$CF_2$—.

Clause 69. The battery of any one of clauses 65 to 67, wherein the fluorinated organic carbonate or the fluorinated organic sulfite comprises one or more —$CF_3$ groups.

Clause 70. The battery of any one of clauses 65 to 67, wherein the fluorinated organic carbonate or the fluorinated organic sulfite comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl.

Clause 71. The battery of any one of clauses 65 to 67, wherein the fluorinated organic carbonate or the fluorinated organic sulfite comprises one or two 1,1,1,3,3,3-hexafluoroisopropyl groups.

Clause 72. The battery of clause 65 wherein the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate.

Clause 73. The battery of clause 65, wherein the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

Clause 74. The battery of any one of clauses 37 to 73, wherein the electrolyte further comprises an alkaline salt.

Clause 75. The battery of clause 74, wherein the alkaline salt is dissolved in the solvent component, wherein the concentration of the alkaline salt is between about 1 M and about 1.5 M.

Clause 76. The battery of clause 74, wherein the alkaline salt is dissolved in the solvent component, wherein the concentration of the alkaline salt is about 1 M, about 1.1 M, about 1.2 M, about 1.3 M, about 1.4 M, or about 1.5 M. In some embodiments, the concentration of the alkaline salt is about 0.5 M. In some embodiments, the concentration of the alkaline salt is about 0.6 M. In some embodiments, the concentration of the alkaline salt is about 0.7 M. In some embodiments, the concentration of the alkaline salt is about 0.8 M. In some embodiments, the concentration of the alkaline salt is about 0.9 M. In some embodiments, the concentration of the alkaline salt is about 1 M. In some embodiments, the concentration of the alkaline salt is about 1.1 M. In some embodiments, the concentration of the alkaline salt is about 1.2 M. In some embodiments, the concentration of the alkaline salt is about 1.3 M. In some embodiments, the concentration of the alkaline salt is about 1.4 M. In some embodiments, the concentration of the alkaline salt is about 1.5 M. In some embodiments, the concentration of the alkaline salt is about 1.6 M. In some embodiments, the concentration of the alkaline salt is about 1.7 M. In some embodiments, the concentration of the alkaline salt is about 1.8 M. In some embodiments, the concentration of the alkaline salt is about 1.9 M. In some embodiments, the concentration of the alkaline salt is about 2 M.

Clause 77. The battery of any one of clauses 74 to 76, wherein the alkaline salt is a lithium salt.

Clause 78. The battery of clause 77, wherein the lithium salt is $LiPF_6$. In some embodiments, the lithium salt is LiFSI (lithium bis(fluorosulfonyl) imide. In some embodiments, the lithium salt is LiTFSI (lithium Bis(trifluoromethanesulfonyl) imide. In some embodiments, the lithium salt is LiBOB (lithium bis(oxalato) borate.

Clause 79. The battery of any one of clauses 37 to 78, wherein the cathode comprises a metal selected from nickel, manganese, and cobalt. In some embodiments, the cathode comprises a transition metal.

Clause 80. The battery of any one of clauses 37 to 78, wherein the cathode comprises between about 70% and about 90% nickel. In some embodiments, the cathode comprises about 65% nickel. In some embodiments, the cathode comprises about 66% nickel. In some embodiments, the cathode comprises about 67% nickel. In some embodiments, the cathode comprises about 68% nickel. In some embodiments, the cathode comprises about 69% nickel. In some embodiments, the cathode comprises about 70% nickel. In some embodiments, the cathode comprises about 71% nickel. In some embodiments, the cathode comprises about 72% nickel. In some embodiments, the cathode comprises about 73% nickel. In some embodiments, the cathode comprises about 74% nickel. In some embodiments, the cathode comprises about 75% nickel. In some embodiments, the cathode comprises about 76% nickel. In some embodiments, the cathode comprises about 77% nickel. In some embodiments, the cathode comprises about 78% nickel. In some embodiments, the cathode comprises about 79% nickel. In some embodiments, the cathode comprises about 80% nickel. In some embodiments, the cathode comprises about 81% nickel. In some embodiments, the cathode comprises about 82% nickel. In some embodiments, the cathode comprises about 83% nickel. In some embodiments, the cathode comprises about 84% nickel. In some embodiments, the cathode comprises about 85% nickel. In some embodiments, the cathode comprises about 86% nickel. In some embodiments, the cathode comprises about 87% nickel. In some embodiments, the cathode comprises about 88% nickel. In some embodiments, the cathode comprises about 89% nickel. In some embodiments, the cathode comprises about 90% nickel. In some embodiments, the cathode comprises about 91% nickel. In some embodiments, the cathode comprises about 92% nickel. In some embodiments, the cathode comprises about 93% nickel. In some embodiments, the cathode comprises about 94% nickel. In some embodiments, the cathode comprises about 95% nickel.

Clause 81. The battery of any one of clauses 37 to 78, wherein the cathode comprises between about 1% and about 15% manganese. In some embodiments, the cathode comprises about 1% manganese. In some embodiments, the cathode comprises about 2% manganese. In some embodiments, the cathode comprises about 3% manganese. In some embodiments, the cathode comprises about 4% manganese. In some embodiments, the cathode comprises about 5% manganese. In some embodiments, the cathode comprises about 6% manganese. In some embodiments, the cathode comprises about 7% manganese. In some embodiments, the cathode comprises about 8% manganese. In some embodiments, the cathode comprises about 9% manganese. In some embodiments, the cathode comprises about 10% manganese. In some embodiments, the cathode comprises about 11% manganese. In some embodiments, the cathode comprises about 12% manganese. In some embodiments, the cathode comprises about 13% manganese. In some embodiments, the cathode comprises about 14% manganese. In some embodiments, the cathode comprises about 15% manganese.

Clause 82. The battery of any one of clauses 37 to 78, wherein the cathode comprises between about 1% and about 15% cobalt. In some embodiments, the cathode comprises about 1% cobalt. In some embodiments, the cathode comprises about 2% cobalt. In some embodiments, the cathode comprises about 3% cobalt. In some embodiments, the cathode comprises about 4% cobalt. In some embodiments, the cathode comprises about 5% cobalt. In some embodiments, the cathode comprises about 6% cobalt. In some embodiments, the cathode comprises about 7% cobalt. In some embodiments, the cathode comprises about 8% cobalt. In some embodiments, the cathode comprises about 9% cobalt. In some embodiments, the cathode comprises about 10% cobalt. In some embodiments, the cathode comprises about 11% cobalt. In some embodiments, the cathode comprises about 12% cobalt. In some embodiments, the cathode comprises about 13% cobalt. In some embodiments, the cathode comprises about 14% cobalt. In some embodiments, the cathode comprises about 15% cobalt.

Clause 83. The battery of any one of clauses 37 to 78, wherein the cathode comprises about 80% nickel, about 10% manganese, and about 10% cobalt. In some embodiments, the cathode comprises about 80% nickel, between about 1% and about 10% manganese, and between about 10% and about 1% cobalt. In some embodiments, the cathode comprises about 65% nickel, and the weight ratio of manganese to cobalt ranges from about 99:1 to about 1:99. In some embodiments, the cathode comprises about 66% nickel, and the weight ratio of manganese to cobalt ranges from about 99:1 to about 1:99. In some embodiments, the cathode comprises about 67% nickel, and the weight ratio of manganese to cobalt ranges from about 99:1 to about 1:99. In some embodiments, the cathode comprises about 68% nickel, and the weight ratio of manganese to cobalt ranges from about 99:1 to about 1:99. In some embodiments, the cathode comprises about 69% nickel, and the weight ratio of manganese to cobalt ranges from about 99:1 to about 1:99. In some embodiments, the cathode comprises about 70% nickel, and the weight ratio of manganese to cobalt ranges from about 99:1 to about 1:99. In some embodiments, the cathode comprises about 71% nickel, and the weight ratio of manganese to cobalt ranges from about 99:1 to about 1:99. In some embodiments, the cathode comprises about 72% nickel, and the weight ratio of manganese to cobalt ranges from about 99:1 to about 1:99. In some embodiments, the cathode comprises about 73% nickel, and the weight ratio of manganese to cobalt ranges from about 99:1 to about 1:99. In some embodiments, the cathode comprises about 74% nickel, and the weight ratio of manganese to cobalt ranges from about 99:1 to about 1:99. In some embodiments, the cathode comprises about 75% nickel, and the weight ratio of manganese to cobalt ranges from about 99:1 to about 1:99. In some embodiments, the cathode comprises about 76% nickel, and the weight ratio of manganese to cobalt ranges from about 99:1 to about 1:99. In some embodiments, the cathode comprises about 77% nickel, and the weight ratio of manganese to cobalt ranges from about 99:1 to about 1:99. In some embodiments, the cathode comprises about 78% nickel, and the weight ratio of manganese to cobalt ranges from about 99:1 to about 1:99. In some embodiments, the cathode comprises about 79% nickel, and the weight ratio of manganese to cobalt ranges from about 99:1 to about 1:99. In some embodiments, the cathode comprises about 80% nickel, and the weight ratio of manganese to cobalt ranges from about 99:1 to about 1:99. In some embodiments, the cathode comprises about 81% nickel, and the weight ratio of manganese to cobalt ranges from about 99:1 to about 1:99. In some embodiments, the cathode comprises about 82% nickel, and the weight ratio of manganese to cobalt ranges from about 99:1 to about 1:99. In some embodiments, the cathode comprises about 83% nickel, and the weight ratio of manganese to cobalt ranges from about 99:1 to about 1:99. In some embodiments, the cathode comprises about 84% nickel, and the weight ratio of manganese to cobalt ranges from about 99:1 to about 1:99. In some embodiments, the cathode comprises about 85% nickel, and the weight ratio of manganese to cobalt ranges from about 99:1 to about 1:99. In some embodiments, the cathode comprises about 86% nickel, and the weight ratio of manganese to cobalt ranges from about 99:1 to about 1:99. In some embodiments, the cathode comprises about 87% nickel, and the weight ratio of manganese to cobalt ranges from about 99:1 to about 1:99. In some embodiments, the cathode comprises about 88% nickel, and the weight ratio of manganese to cobalt ranges from about 99:1 to about 1:99. In some embodiments, the cathode comprises about 89% nickel, and the weight ratio of manganese to cobalt ranges from about 99:1 to about 1:99. In some embodiments, the cathode comprises about 90% nickel, and the weight ratio of manganese to cobalt ranges from about 99:1 to about 1:99. In some embodiments, the cathode comprises about 91% nickel, and the weight ratio of manganese to cobalt ranges from about 99:1 to about 1:99. In some embodiments, the cathode comprises about 92% nickel, and the weight ratio of manganese to cobalt ranges from about 99:1 to about 1:99. In some embodiments, the cathode comprises about 93% nickel, and the weight ratio of manganese to cobalt ranges from about 99:1 to about 1:99. In some embodiments, the cathode comprises about 94% nickel, and the weight ratio of manganese to cobalt ranges from about 99:1 to about 1:99. In some embodiments, the cathode comprises about 95% nickel, and the weight ratio of manganese to cobalt ranges from about 99:1 to about 1:99.

In some embodiments, the cathode comprises about 96% to 99% nickel, and the weight ratio of manganese to cobalt ranges from about 99:1 to about 1:99.

Clause 84. The battery of any one of clauses 37 to 78, wherein the cathode comprises about 90% nickel, about 5% manganese, and about 5% cobalt.

Clause 85. The battery of any one of clauses 37 to 84, wherein the anode comprises between about 2% and about 75% silicon. In some embodiments, the anode comprises about 1% silicon. In some embodiments, the anode comprises about 2% silicon. In some embodiments, the anode comprises about 3% silicon. In some embodiments, the anode comprises about 4% silicon. In some embodiments, the anode comprises about 5% silicon. In some embodiments, the anode comprises about 6% silicon. In some embodiments, the anode comprises about 7% silicon. In some embodiments, the anode comprises about 8% silicon. In some embodiments, the anode comprises about 9% silicon. In some embodiments, the anode comprises about 10% silicon. In some embodiments, the anode comprises about 11% silicon. In some embodiments, the anode comprises about 12% silicon. In some embodiments, the anode comprises about 13% silicon. In some embodiments, the anode comprises about 14% silicon. In some embodiments, the anode comprises about 15% silicon. In some embodiments, the anode comprises about 16% silicon. In some embodiments, the anode comprises about 17% silicon. In some embodiments, the anode comprises about 18% silicon. In some embodiments, the anode comprises about 19% silicon. In some embodiments, the anode comprises about 20% silicon. In some embodiments, the anode comprises about 21% silicon. In some embodiments, the anode comprises about 22% silicon. In some embodiments, the anode comprises about 23% silicon. In some embodiments, the anode comprises about 24% silicon. In some embodiments, the anode comprises about 25% silicon. In some embodiments, the anode comprises about 26% silicon. In some embodiments, the anode comprises about 27% silicon. In some embodiments, the anode comprises about 28% silicon. In some embodiments, the anode comprises about 29% silicon. In some embodiments, the anode comprises about 30% silicon. In some embodiments, the anode comprises about 31% silicon. In some embodiments, the anode comprises about 32% silicon. In some embodiments, the anode comprises about 33% silicon. In some embodiments, the anode comprises about 34% silicon. In some embodiments, the anode comprises about 35% silicon. In some embodiments, the anode comprises about 36% silicon. In some embodiments, the anode comprises about 37% silicon. In some embodiments, the anode comprises about 38% silicon. In some embodiments, the anode comprises about 39% silicon. In some embodiments, the anode comprises about 40% silicon. In some embodiments, the anode comprises between about 5% and about 10% of silicon. In some embodiments, the anode comprises between about 10% and about 15% of silicon. In some embodiments, the anode comprises between about 15% and about 20% of silicon. In some embodiments, the anode comprises between about 20% and about 25% of silicon. In some embodiments, the anode comprises between about 25% and about 30% of silicon. In some embodiments, the anode comprises between about 30% and about 35% of silicon. In some embodiments, the anode comprises between about 35% and about 40% of silicon. In some embodiments, the anode comprises between about 40% and about 45% of silicon. In some embodiments, the anode comprises between about 45% and about 50% of silicon. In some embodiments, the anode comprises between about 50% and about 55% of silicon. In some embodiments, the anode comprises between about 55% and about 60% of silicon. In some embodiments, the anode comprises between about 60% and about 65% of silicon. In some embodiments, the anode comprises between about 65% and about 70% of silicon.

Clause 86. The battery of any one of clauses 37 to 84, wherein the anode comprises between about 2% and about 75% of a silicon oxide graphite composite. In some embodiments, the anode comprises about 1% silicon oxide graphite composite. In some embodiments, the anode comprises about 2% silicon oxide graphite composite. In some embodiments, the anode comprises about 3% silicon oxide graphite composite. In some embodiments, the anode comprises about 4% silicon oxide graphite composite. In some embodiments, the anode comprises about 5% silicon oxide graphite composite. In some embodiments, the anode comprises about 6% silicon oxide graphite composite. In some embodiments, the anode comprises about 7% silicon oxide graphite composite. In some embodiments, the anode comprises about 8% silicon oxide graphite composite. In some embodiments, the anode comprises about 9% silicon oxide graphite composite. In some embodiments, the anode comprises about 10% silicon oxide graphite composite. In some embodiments, the anode comprises about 11% silicon oxide graphite composite. In some embodiments, the anode comprises about 12% silicon oxide graphite composite. In some embodiments, the anode comprises about 13% silicon oxide graphite composite. In some embodiments, the anode comprises about 14% silicon oxide graphite composite. In some embodiments, the anode comprises about 15% silicon oxide graphite composite. In some embodiments, the anode comprises about 16% silicon oxide graphite composite. In some embodiments, the anode comprises about 17% silicon oxide graphite composite. In some embodiments, the anode comprises about 18% silicon oxide graphite composite. In some embodiments, the anode comprises about 19% silicon oxide graphite composite. In some embodiments, the anode comprises about 20% silicon oxide graphite composite. In some embodiments, the anode comprises about 21% silicon oxide graphite composite. In some embodiments, the anode comprises about 22% silicon oxide graphite composite. In some embodiments, the anode comprises about 23% silicon oxide graphite composite. In some embodiments, the anode comprises about 24% silicon oxide graphite composite. In some embodiments, the anode comprises about 25% silicon oxide graphite composite. In some embodiments, the anode comprises about 26% silicon oxide graphite composite. In some embodiments, the anode comprises about 27% silicon oxide graphite composite. In some embodiments, the anode comprises about 28% silicon oxide graphite composite. In some embodiments, the anode comprises about 29% silicon oxide graphite composite. In some embodiments, the anode comprises about 30% silicon oxide graphite composite. In some embodiments, the anode comprises about 31% silicon oxide graphite composite. In some embodiments, the anode comprises about 32% silicon oxide graphite composite. In some embodiments, the anode comprises about 33% silicon oxide graphite composite. In some embodiments, the anode comprises about 34% silicon oxide graphite composite. In some embodiments, the anode comprises about 35% silicon oxide graphite composite. In some embodiments, the anode comprises about 36% silicon oxide graphite composite. In some embodiments, the anode comprises about 37% silicon oxide graphite composite. In some embodiments, the anode comprises about 38% silicon oxide graphite composite. In some embodiments, the anode comprises about 39% silicon oxide graphite composite. In some embodiments, the anode comprises about 40% silicon oxide graphite composite. In some embodiments, the anode comprises between about 5% and about 10% of silicon oxide graphite composite. In some embodiments, the anode comprises between about 10% and about 15% of silicon oxide graphite composite. In some embodiments, the anode comprises between about 15% and about 20% of silicon oxide graphite composite. In some embodiments, the anode comprises between about 20% and about 25% of silicon oxide graphite composite. In some embodiments, the anode comprises between about 25% and about 30% of silicon oxide graphite composite. In some embodiments, the anode comprises between about 30% and about 35% of silicon oxide graphite composite. In some embodiments, the anode comprises between about 35% and about 40% of silicon oxide graphite composite. In some embodiments, the anode comprises between about 40% and about 45% of silicon oxide graphite composite. In some embodiments, the anode comprises between about 45% and about 50% of silicon oxide graphite composite. In some embodiments, the anode comprises between about 50% and about 55% of silicon oxide graphite composite. In some embodiments, the anode comprises between about 55% and about 60% of silicon oxide graphite composite. In some embodiments, the anode comprises between about 60% and about 65% of silicon oxide graphite composite. In some embodiments, the anode comprises between about 65% and about 70% of silicon oxide graphite composite. In some embodiments, the anode comprises between about 70% and about 75% of silicon oxide graphite composite.

Clause 87. The battery of any one of clauses 37 to 84, wherein the anode comprises between about 2% and about 75% of amorphous silicon graphite composite. In some embodiments, the anode comprises about 1% amorphous silicon graphite composite. In some embodiments, the anode comprises about 2% amorphous silicon graphite composite. In some embodiments, the anode comprises about 3% amorphous silicon graphite composite. In some embodiments, the anode comprises about 4% amorphous silicon graphite composite. In some embodiments, the anode comprises about 5% amorphous silicon graphite composite. In some embodiments, the anode comprises about 6% amorphous silicon graphite composite. In some embodiments, the anode comprises about 7% amorphous silicon graphite composite. In some embodiments, the anode comprises about 8% amorphous silicon graphite composite. In some embodiments, the anode comprises about 9% amorphous silicon graphite composite. In some embodiments, the anode comprises about 10% amorphous silicon graphite composite. In some embodiments, the anode comprises about 11% amorphous silicon graphite composite. In some embodiments, the anode comprises about 12% amorphous silicon graphite composite. In some embodiments, the anode comprises about 13% amorphous silicon graphite composite. In some embodiments, the anode comprises about 14% amorphous silicon graphite composite. In some embodiments, the anode comprises about 15% amorphous silicon graphite composite. In some embodiments, the anode comprises about 16% amorphous silicon graphite composite. In some embodiments, the anode comprises about 17% amorphous silicon graphite composite. In some embodiments, the anode comprises about 18% amorphous silicon graphite composite. In some embodiments, the anode comprises about 19% amorphous silicon graphite composite. In some embodiments, the anode comprises about 20% amorphous silicon graphite composite. In some embodiments, the anode comprises about 21% amorphous silicon graphite composite. In some embodiments, the anode comprises about 22% amorphous silicon graphite composite. In some embodiments, the anode comprises about 23% amorphous silicon graphite composite. In some embodiments, the anode comprises about 24% amorphous silicon graphite composite. In some embodiments, the anode comprises about 25% amorphous silicon graphite composite. In some embodiments, the anode comprises about 26% amorphous silicon graphite composite. In some embodiments, the anode comprises about 27% amorphous silicon graphite composite. In some embodiments, the anode comprises about 28% amorphous silicon graphite composite. In some embodiments, the anode comprises about 29% amorphous silicon graphite composite. In some embodiments, the anode comprises about 30% amorphous silicon graphite composite. In some embodiments, the anode comprises about 31% amorphous silicon graphite composite. In some embodiments, the anode comprises about 32% amorphous silicon graphite composite. In some embodiments, the anode comprises about 33% amorphous silicon graphite composite. In some embodiments, the anode comprises about 34% amorphous silicon graphite composite. In some embodiments, the anode comprises about 35% amorphous silicon graphite composite. In some embodiments, the anode comprises about 36% amorphous silicon graphite composite. In some embodiments, the anode comprises about 37% amorphous silicon graphite composite. In some embodiments, the anode comprises about 38% amorphous silicon graphite composite. In some embodiments, the anode comprises about 39% amorphous silicon graphite composite. In some embodiments, the anode comprises about 40% amorphous silicon graphite composite. In some embodiments, the anode comprises between about 5% and about 10% of amorphous silicon graphite composite. In some embodiments, the anode comprises between about 10% and about 15% of amorphous silicon graphite composite. In some embodiments, the anode comprises between about 15% and about 20% of amorphous silicon graphite composite. In some embodiments, the anode comprises between about 20% and about 25% of amorphous silicon graphite composite. In some embodiments, the anode comprises between about 25% and about 30% of amorphous silicon graphite composite. In some embodiments, the anode comprises between about 30% and about 35% of amorphous silicon graphite composite. In some embodiments, the anode comprises between about 35% and about 40% of amorphous silicon graphite composite. In some embodiments, the anode comprises between about 40% and about 45% of amorphous silicon graphite composite. In some embodiments, the anode comprises between about 45% and about 50% of amorphous silicon graphite composite. In some embodiments, the anode comprises between about 50% and about 55% of amorphous silicon graphite composite. In some embodiments, the anode comprises between about 55% and about 60% of amorphous silicon graphite composite. In some embodiments, the anode comprises between about 60% and about 65% of amorphous silicon graphite composite. In some embodiments, the anode comprises between about 65% and about 70% of amorphous silicon graphite composite. In some embodiments, the anode comprises between about 70% and about 75% of amorphous silicon graphite composite.

Clause 88. The battery of any one of clauses 37 to 87, wherein the battery is rechargeable, and wherein the battery has a cycle life of between about 150 and about 500 cycles. In some embodiments, the battery has a cycle life of between about 150 and about 200 cycles. In some embodiments, the battery has a cycle life of between about 200 and about 250 cycles. In some embodiments, the battery has a cycle life of between about 250 and about 300 cycles. In some embodiments, the battery has a cycle life of between about 300 and about 350 cycles. In some embodiments, the battery has a cycle life of between about 350 and about 400 cycles. In some embodiments, the battery has a cycle life of between about 400 and about 450 cycles. In some embodiments, the battery has a cycle life of between about 450 and about 500 cycles. In some embodiments, the battery has a cycle life of between about 500 and about 550 cycles. In some embodiments, the battery has a cycle life of between about 550 and about 600 cycles. In some embodiments, the battery has a cycle life of between about 600 and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles. In some embodiments, the battery has a cycle life of between about and about cycles.

Clause 89. The battery of clause 88, wherein the battery has a cycle life of at least 200 cycles.

Clause 90. The battery of clause 88, wherein the battery has a cycle life of at least 250 cycles.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Synthesis of Methyl 2,2,2-trifluoroethyl Carbonate

A cooling water jacketed 2 L 3-neck flask equipped with a mechanical stirrer and addition funnel was charged with 2,2,2-trifluoroethanol (150 g, 1.50 mol), methyl chloroformate (146 g, 1.55 mol) and hexafluoroisopropyl methyl ether (470 g). Triethylamine (157 g, 1.55 mol) was added in slowly as to keep the internal temperature less than 30° C. (total addition time 1.5 h). After 2 h, GC indicated 96.1% conversion of the starting alcohol to methyl 2,2,2-trifluoroethyl carbonate.

Example 2: Synthesis of Methyl 1,1,1-trifluoroisopropyl Carbonate

A cooling water jacketed 1 L 3-neck flask equipped with a mechanical stirrer and addition funnel was charged with 1,1,1-trifluoro-2-propanol (114 g, 1.00 mol), methyl chloroformate (94 g, 1.00 mol) and hexafluoroisopropyl methyl ether (200 mL). Triethylamine (102 g, 1.00 mol) was added in slowly as to keep the internal temperature less than 30° C. (total addition time 2 h). After 2 h, GC indicated 96.4% conversion of the starting alcohol to methyl 1,1,1-trifluoroisopropyl carbonate.

Example 3: Synthesis of Methyl 1,1,1,3,3,3-hexafluoroisopropyl Carbonate

A cooling water jacketed 2 L 3-neck flask equipped with a mechanical stirrer and addition funnel was charged with 1,1,1,3,3,3-hexafluoroisopropanol (252 g, 1.50 mol), methyl chloroformate (146 g, 1.55 mol) and hexafluoroisopropyl methyl ether (470 g). Triethylamine (157 g, 1.55 mol) was added in slowly as to keep the internal temperature less than 30° C. (total addition time 1.5 h). After 2 h, GC indicated 98.6% conversion of the starting alcohol to methyl 1,1,1,3,3-hexafluoroisopropyl carbonate.

Example 4: Synthesis of Bis(1,1,1,3,3,3-hexafluoroisopropyl) Sulfite

To 1,1,1,3,3,3-hexafluoroisopropanol (336 g, 2.00 mol) and triethylamine (203 g, 2.00 mol) in hexafluoroisopropyl methyl ether (1.0 kg) was added thionyl chloride (73 mL, 1.0 mol) dropwise at 0° C. keeping the internal temperature under 15° C. (total addition time 1 h) after 2 h, GC indicated 90.6% conversion of starting alcohol to bis(1,1,1,3,3,3-hexafluoroisopropyl) sulfite.

Example 4: Silicon Composite Anode Studies—FEC/FEC Combinations Comparison

Materials: cathode: NMC 811; anode: Si-graphite composite, 10% amorphous Si; baseline electrolyte: 1.2 M $LiPF_6$ in a solvent including 88% ethylene carbonate/ethyl methyl carbonate (EC/EMC 3:7), 10% FEC, and 2% VC (vinylene carbonate).

Cycle Life Test: test vehicle: single-layer-pouch cell. Test protocol: Charge to 4.4 V at 1 C, discharge to 3.0 V at 1 C (electrode loading: 1.26 $mAh/cm^2$ and 1.90 $mAh/cm^2$).

FIG. 1 illustrates the performance improvement in a high temperature silicon anode battery by using an electrolyte including trifluoroethyl-methyl carbonate (F3EMC), vs an electrolyte including fluoro ethylene carbonate (FEC)— F3EMC and combination of FEC/F3EMC outperform FEC alone (F3EMC is carbonate $CF_3CH_2OC(O)OCH_3$; 1C/−1C cycling 4.40-3.00 V; cell type—pouch cell, cycling (@ 45° C.)—4.40 V to 3.00 V, cathode—NMC 811, anode 10% silicon composite).

Figure 2:
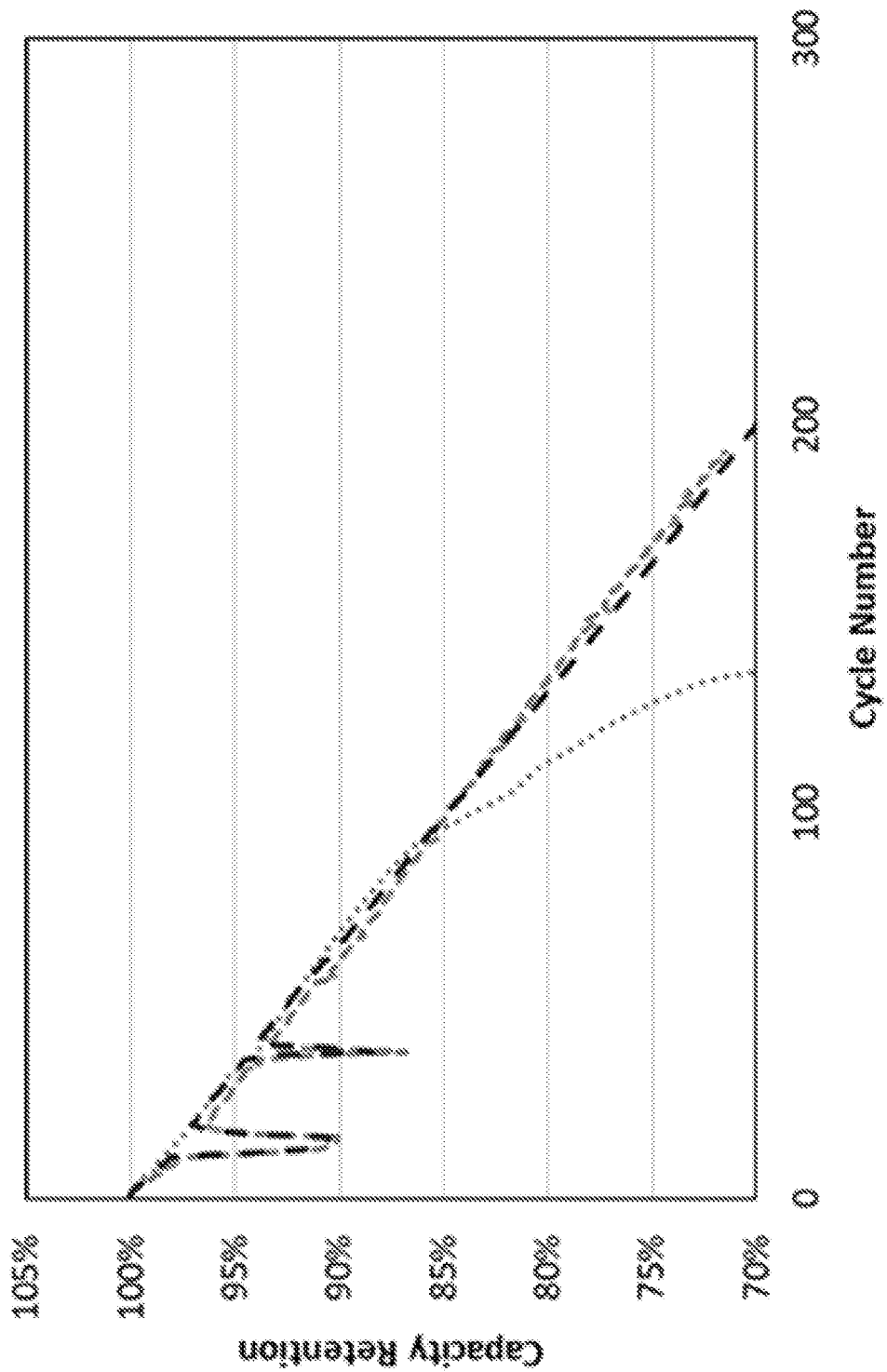
FIG. 2 illustrates the performance improvement at high temperature in a battery containing NMC 811 cathode and silicon composite anode by using an electrolyte including trifluoroethyl acetate ester, vs an electrolyte including FEC.

Legend:
⋯⋯⋯ 1.2 M $LiPF_6$ solution in 88% EC/EMC (3:7), 10% FEC, and 2% VC
− − − 1.2 M $LiPF_6$ solution in 88% EC/EMC (3:7), 3% FEC, 7% F3EMC, and 2% VC
—•—•— 1.2 M $LiPF_6$ solution in 88% EC/EMC (3:7), 10% F3EMC, and 2% VC FIG. 2 illustrates the performance improvement in a high temperature silicon anode battery by using an electrolyte including trifluoroethyl acetate ester, vs an electrolyte including FEC—combination of FEC/trifluoroethyl acetate ester outperform FEC alone (trifluoroethyl acetate ester is $CF_3CH_2OC(O)CH_3$; 1C/−1C cycling 4.40-3.00 V; cell type—pouch cell, cycling (@ 45° C.)—4.40 V to 3.00 V, cathode—NMC 811, anode 10% silicon composite).

Legend:
⋯⋯⋯ 1.2 M $LiPF_6$ solution in 88% EC/EMC (3:7), 10% FEC, and 2% VC (vinylene carbonate)

- - - 1.2 M LiPF$_6$ solution in 83% EC/EMC (3:7), 5% FEC, 10% trifluoroethyl acetate ester, and 2% VC (vinylene carbonate)
- - - - 1.2 M LiPF$_6$ solution in 88% EC/EMC (3:7), 3% FEC, 7% trifluoroethyl acetate ester and 2% VC (vinylene carbonate)

Figure 3:
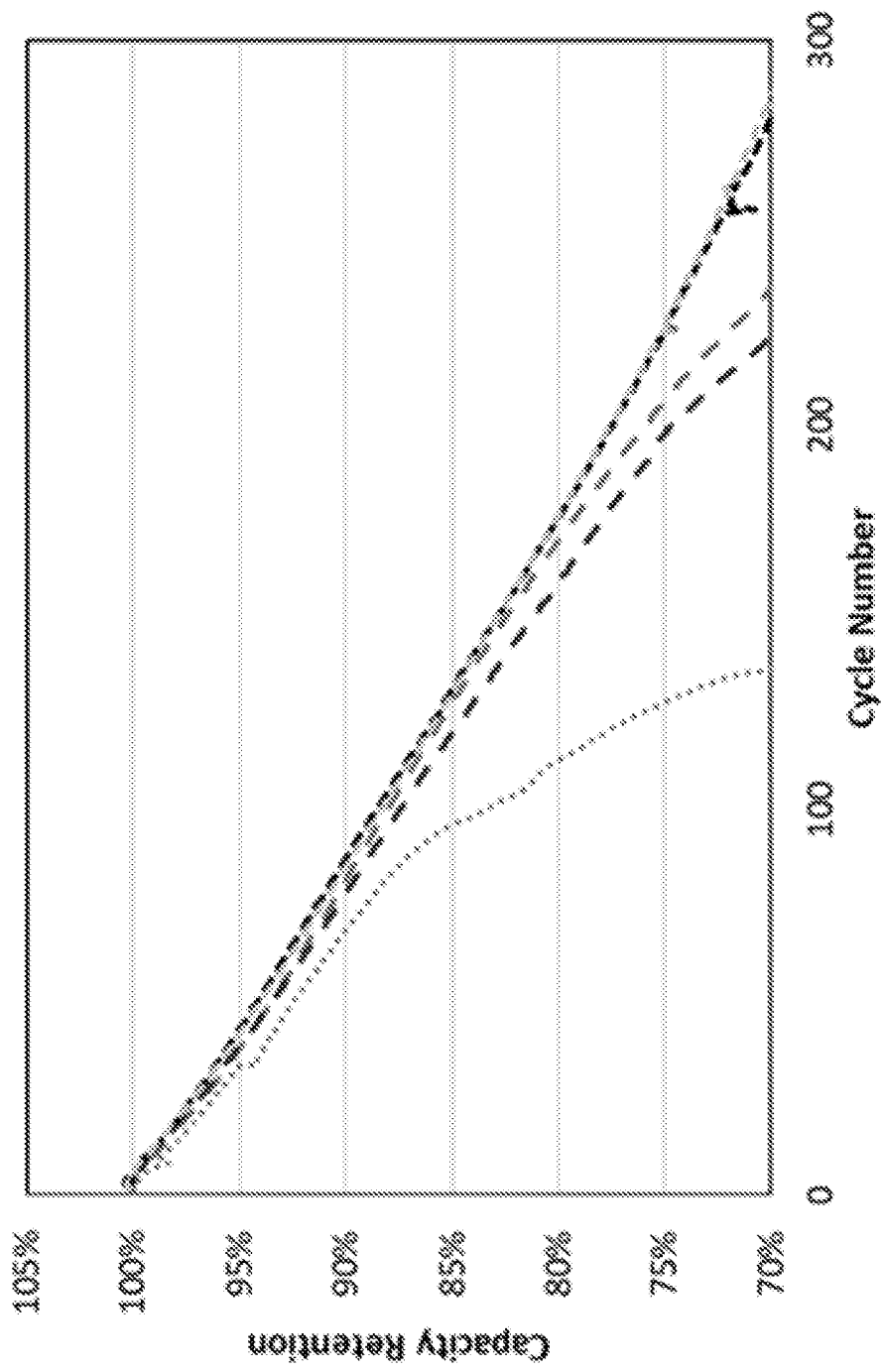
FIG. 3 illustrates the performance improvement at high temperature in a battery containing NMC 811 cathode and silicon composite anode by using an electrolyte including hexafluoro-2-methoxypropane (hexafluoro-2-propyl methyl ether), vs an electrolyte including fluoro ethylene carbonate (FEC).

FIG. 3 illustrates the performance improvement in a high temperature silicon anode battery by using an electrolyte including hexafluoro-2-methoxypropane (hexafluoro-2-propyl methyl ether), vs an electrolyte including fluoro ethylene carbonate (FEC)—hexafluoro-2-methoxypropane without or in combination with FEC outperform FEC alone by >80% (hexafluoro-2-methoxypropane is (CF$_3$)$_2$CHOCH$_3$; 1C/−1C cycling 4.40-3.00 V; cell type—pouch cell, cycling (@ 45° C.)—4.40 V to 3.00 V, cathode—NMC 811, anode 10% silicon composite)

Legend:
······· 1.2 M LiPF$_6$ solution in 88% EC/EMC (3:7), 10% FEC, and 2% VC (vinylene carbonate)
- - - 1.2 M LiPF$_6$ solution in 88% EC/EMC (3:7), 3% FEC, 7% hexafluoro-2-methoxypropane, and 2% VC (vinylene carbonate)
- - - - 1.2 M LiPF$_6$ solution in 88% EC/EMC (3:7), 10% hexafluoro-2-methoxypropane, and 2% VC (vinylene carbonate)

Without wishing to be bound by any particular theory, it appears that, in some embodiments, hexafluoro-2-methoxypropane outperforms F3EMC, which outperforms trifluoroethyl acetate ester, which outperforms FEC.

A number of patent and non-patent publications are cited herein in order to describe the state of the art to which this disclosure pertains. The entire disclosure of each of these publications is incorporated by reference herein.

While certain embodiments of the present disclosure have been described and/or exemplified above, various other embodiments will be apparent to those skilled in the art from the foregoing disclosure. The present disclosure is, therefore, not limited to the particular embodiments described and/or exemplified, but is capable of considerable variation and modification without departure from the scope and spirit of the appended claims.

The invention claimed is:

1. A battery comprising an electrolyte comprising a solvent component, wherein the solvent component comprises a fluorinated compound in an amount between about 1 ppm and about 60 wt. %, wherein the fluorinated compound has Formula III:

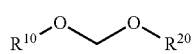

Formula III wherein R$^{10}$ and R$^{20}$ are independently selected from C$_1$-C$_6$ alkyl, C$_1$-C$_8$ alkyl, cycloalkyl, aryl, fully or partially fluorinated C$_1$-C$_6$ alkyl, fully or partially fluorinated C$_1$-C$_8$ alkyl, fully or partially fluorinated cycloalkyl, and fully or partially fluorinated aryl, and wherein the fluorinated compound comprises two or more —CF$_3$ groups.

2. The battery of claim 1, wherein R$^{10}$ comprises one or more —CF$_3$ groups.

3. The battery of claim 1, wherein R$^{10}$ and R$^{20}$ are identical.

4. The battery of claim 1, wherein the compound of Formula III is a compound of any one of Formula 300 or Formula 301:

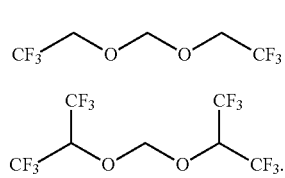

Formula 300

Formula 301

5. The battery of claim 1, wherein the fluorinated compound comprises one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl.

6. The battery of claim 1, wherein the solvent component comprises the fluorinated compound in an amount between about 2 wt. % and about 40 wt. %.

7. The battery of claim 1, wherein the electrolyte is a non-aqueous electrolyte, wherein the solvent component further comprises one or more of a partially fluorinated organic carbonate and non-fluorinated organic carbonate.

8. The battery of claim 1, wherein the electrolyte further comprises a fluorinated organic carbonate or a fluorinated organic sulfite comprising one or more groups selected from 2,2,2-trifluoroethyl, 1,1,1-trifluoroisopropyl, 1,1,1,3,3,3-hexafluoroisopropyl, 3,3,3-trifluoropropyl, 2-fluoroethyl, 2,2-difluoroethyl, 3-fluoropropyl, 3,3-difluoropropyl, 2,2,3,3,3-pentafluoropropyl, 4,4,4-trifluorobutyl, 1,1,1,3,3-pentafluoroisopropyl, and 5,5,5-trifluoropentyl.

9. The battery of claim 8, wherein the fluorinated organic carbonate is selected from methyl (2,2,2-trifluoroethyl) carbonate, methyl (1,1,1-trifluoroisopropyl) carbonate, methyl (1,1,1,3,3,3-hexafluoroisopropyl) carbonate, methyl (3,3,3-trifluoropropyl) carbonate, methyl (2-fluoroethyl) carbonate, methyl (2,2-difluoroethyl) carbonate, methyl (3-fluoropropyl) carbonate, methyl (3,3-difluoropropyl) carbonate, methyl (2,2,3,3,3-pentafluoropropyl) carbonate, methyl (4,4,4-trifluorobutyl) carbonate, methyl (1,1,1,3,3-pentafluoroisopropyl) carbonate, and methyl (5,5,5-trifluoropentyl) carbonate, wherein the fluorinated organic sulfite is selected from bis-(2,2,2-trifluoroethyl) sulfite, bis-(1,1,1-trifluoroisopropyl) sulfite, and bis-(1,1,1,3,3,3-hexafluoroisopropyl) sulfite.

10. The battery of claim 1, wherein the electrolyte further comprises an alkaline salt, wherein the alkaline salt is dissolved in the solvent component, wherein the concentration of the alkaline salt is between about 1 M and about 1.5 M.

11. The battery of claim 10, wherein the alkaline salt is a lithium salt.

12. The battery of claim 1 further comprising a cathode comprising a metal selected from nickel, manganese, and cobalt.

13. The battery of claim 12, wherein the cathode comprises a stoichiometric ratio of between about 0.7 and about 0.9 nickel, between about 0.01 and about 0.15 manganese, and between about 0.01 and about 0.15 cobalt relative to the transition metals in the cathode.

14. The battery of claim 1, further comprising an anode comprising between about 2 wt. % and about 75 wt. % silicon.

15. The battery of claim 1, wherein the battery is rechargeable, and wherein the battery has a cycle life of between about 150 and about 500 cycles.

16. The battery of claim 1, wherein $R^{20}$ comprises one or more —$CF_3$ groups.

17. The battery of claim 1, further comprising an anode comprising between 2 wt. % and 70 wt. % of a silicon oxide graphite composite.

18. The battery of claim 1, further comprising an anode comprising between 2 wt. % and 70 wt. % of amorphous silicon graphite composite.

19. The battery of claim 1, further comprising an anode comprising between 5 wt. % and 15 wt. % of silicon oxide graphite composite or amorphous silicon graphite composite.

20. The battery of claim 1, further comprising an anode comprising a material selected from lithium metal, a lithium metal alloy, lithium titanate, and lithiated tin oxide.

\* \* \* \* \*